(12) United States Patent
Flugelman

(10) Patent No.: US 7,887,581 B2
(45) Date of Patent: *Feb. 15, 2011

(54) METHODS OF HEMODIALYSIS UTILIZING GRAFTS COATED WITH CELLS EXPRESSING HUMAN FIBULIN-5

(75) Inventor: Moshe Flugelman, Haifa (IL)

(73) Assignee: Multi-Gene Vascular Systems, Ltd., Haifa (IL)

( * ) Notice: Subject to any disclaimer, the term of this patent is extended or adjusted under 35 U.S.C. 154(b) by 885 days.

This patent is subject to a terminal disclaimer.

(21) Appl. No.: 11/649,588

(22) Filed: Jan. 3, 2007

(65) Prior Publication Data

US 2007/0190037 A1    Aug. 16, 2007

Related U.S. Application Data

(60) Division of application No. 10/164,219, filed on Jun. 4, 2002, now Pat. No. 7,175,658, which is a continuation-in-part of application No. 09/620,227, filed on Jul. 20, 2000, now abandoned.

(51) Int. Cl.
*A61F 2/06* (2006.01)
*A61K 48/00* (2006.01)
*A01N 63/00* (2006.01)
*C12N 15/00* (2006.01)

(52) U.S. Cl. .................. 623/1.41; 623/1.42; 623/1.43; 514/44 R; 424/93.21; 435/320.1

(58) Field of Classification Search ....................... None
See application file for complete search history.

(56) References Cited

U.S. PATENT DOCUMENTS

| | | | |
|---|---|---|---|
| 5,131,907 A | 7/1992 | Williams et al. ............... 600/36 |
| 5,591,227 A | 1/1997 | Dinh et al. ...................... 623/1 |
| 5,674,722 A | 10/1997 | Mulligan et al. .......... 435/172.3 |
| 5,733,327 A | 3/1998 | Igaki et al. ...................... 623/1 |
| 5,736,360 A | 4/1998 | Gaulton et al. .............. 435/69.1 |
| 5,785,965 A | 7/1998 | Pratt et al. ................ 424/93.21 |
| 5,872,234 A | 2/1999 | Bandman et al. ........... 536/23.1 |
| 5,899,935 A | 5/1999 | Ding ............................... 623/1 |
| 5,925,564 A | 7/1999 | Schwartz et al. ............. 435/325 |
| 5,941,868 A | 8/1999 | Kaplan et al. ................ 604/500 |
| 6,001,350 A | 12/1999 | Mulligan et al. .......... 424/93.21 |
| 6,077,987 A | 6/2000 | Breitbart et al. ................ 623/11 |
| 6,364,856 B1 | 4/2002 | Ding et al. .............. 604/103.02 |
| 6,375,929 B1 | 4/2002 | Thomas, Jr. et al. ........... 424/9.2 |
| 6,403,635 B1 | 6/2002 | Kinsella et al. ............... 514/449 |
| 6,425,881 B1 | 7/2002 | Kaesemeyer .................. 604/93 |
| 6,554,857 B1 | 4/2003 | Zilla et al. ................... 623/1.23 |
| 6,589,534 B1 | 7/2003 | Shaul et al. ............... 424/227.1 |
| 6,716,242 B1 | 4/2004 | Altman ...................... 623/1.42 |
| 6,846,647 B1 | 1/2005 | Honjo et al. ................... 435/29 |
| 6,918,929 B2 | 7/2005 | Udipi et al. ................. 623/1.42 |
| 6,939,376 B2 | 9/2005 | Shulze et al. .............. 623/1.42 |
| 2003/0118551 A1 | 6/2003 | Hall et al. .................. 424/93.2 |
| 2003/0229393 A1 | 12/2003 | Kutryk et al. .............. 623/1.46 |
| 2004/0126788 A1 | 7/2004 | Schiemann et al. ............. 435/6 |
| 2006/0079439 A1 | 4/2006 | Li et al. .......................... 514/2 |
| 2006/0275338 A1 | 12/2006 | Flugelman .................. 424/423 |
| 2008/0269472 A1 | 10/2008 | Flugelman ................. 536/23.5 |

FOREIGN PATENT DOCUMENTS

| | | |
|---|---|---|
| EP | 1 568 375 A1 | 8/2005 |
| WO | WO 92/11895 | 7/1992 |
| WO | WO 95/05866 | 3/1995 |
| WO | WO 96/08286 | 3/1996 |
| WO | WO 98/56312 | 12/1998 |
| WO | WO 99/55863 | 11/1999 |
| WO | WO 99/55864 | 11/1999 |
| WO | WO 02/07646 A2 | 1/2002 |
| WO | WO 2005/093057 A1 | 10/2005 |
| WO | WO 2005/099695 | 10/2005 |
| WO | WO 2006/082763 A1 | 8/2006 |
| WO | WO 2007/088418 | 8/2007 |

OTHER PUBLICATIONS

Anderson *Nature*, 392:25-30 (1998).
Clowes *Circulation*, 93:1319-1320 (1996).
Cosset et al. *Gene Therapy*, 3(11):946-956 (1996).
Darling et al. *Am. J. Surg.*, 123(4):472-479 (1972).
Dichek et al. *Circulation*, 93:304-309 (1996).
Dunn et al. *Circulation*, 93:1439-1446 (1996).
Edelman *Circ. Res.*, 85:1115-1117 (1999).
Eickhoff et al. *J. Vasc. Surg.*, 6(5):506-511 (1987).

(Continued)

*Primary Examiner*—Robert M Kelly
(74) *Attorney, Agent, or Firm*—Mintz Levin Cohn Ferris Glovsky and Popeo, P.C.; Ivor R. Elrifi; Matthew Pavao

(57) ABSTRACT

The present relates to artificial vascular grafts and for methods for performing hemodialysis with the same. The grafts comprise an inner surface on which cells genetically altered to express or over-express one or more cell adhesion factors, such as fibulin-5, or one or more cell adhesion factors and one or more cell proliferation growth factors, such as VEGF, are seeded and cultured.

5 Claims, 5 Drawing Sheets

OTHER PUBLICATIONS

Falk et al. *J. Vasc. Surg.*, 27(5):902-909 (1998).
Folkman *Circulation*, 97:1108-1110 (1998).
Gillis-Haegerstrand et al. *J. Vasc. Surg.*, 24(2):226-234 (1996).
Hanahan *Science*, 277:48-50 (1997).
Huber et al. *J. Vasc. Surg.*, 22(6):795-803 (1995).
Leung et al. *Science*, 246:1306-1309 (1989).
Londrey et al. *J. Vasc. Surg.*, 13(5):631-636 (1991).
Magometschnigg et al. *J. Vasc. Surg.*, 15(3):527-535 (1992).
Meinhart et al. *ASAIO J.*, 43(5):M515-M521 (1997).
Mulligan *Science*, 260:926-932 (1993).
Nakamura et al. *J. Biol. Chem.*, 274(32):22476-22483 (1999).
Noishiki et al. *Nat. Med.*, 2(1):90-93 (1996).
Pasic et al. *Circulation*, 92:2605-2616 (1995).
Rutherford et al. *Vasc. Surg.*, Third Edition, W.B. Saunders Co., pp. 501-510 (1989).
Sapienza et al. *J. Surg. Res.*, 75(1):24-29 (1998).
Vaisman et al. *J. Biol. Chem.*, 265(32):19461-19466 (1990).
Van Belle et al. *Circulation*, 95:438-448 (1997).
Veterans Adminstration Cooperative Study Group 141 *Arch. Surg.*, 123(4):434-438 (1988).
GenBank Accession No. AB021221.1, 3 pages (Jun. 1999).
GenBank Accession No. AF112152.1, 3 pages (Aug. 1999).
GenBank Accession No. D14012.1, 3 pages (Feb. 2003).
GenBank Accession No. J00114.1. 3 pages, (Nov. 1994).
GenBank Accession No. M15524.1, 3 pages (Nov. 1994).
GenBank Accession No. M27968.1, 4 pages (Nov. 1994).
GenBank Accession No. NM_000477.5, 6 pages (Feb. 2009).
GenBank Accession No. NM_000638.3, 5 pages (Feb. 2009).
GenBank Accession No. NM_001795.3, 7 pages (Jan. 2009).
GenBank Accession No. NM_005530.3, 15 pates (Dec. 2008).
GenBank Accession No. NM_006329.3, 7 pages (Feb. 2009).
GenBank Accession No. S67291, 3 pages (Mar. 2001).
GenBank Accession No. X02761.1, 6 pages (Apr. 2005).
GenBank Accession No. XM_065759.1, 3 pages (Apr. 2003).
Eck et al., Goodman & Gilman's The Pharmacological Basis of Therapeutics, McGraw-Hill, New York, NY, pp. 77-101 (1996).
Stryer, *Biochemistry*, $3^{rd}$ Ed., by WH Freeman & Co., New York, NY, p. 277 (1988).
Chen et al., "Restenosis: Emerging molecular targets. Going beyond drug-eluting stents", *Drug Dis. Today: Disease Mechanisms*, 2(1):1-9 (2005).
Jaschke et al., "Local statin therapy differentially inteferes with smooth muscle and endothelial cell proliferation and reduces neointima on a drug-eluting stent platform", *Card. Res.*, 68(3):483-492 (2005).
Spencer et al., "Altered vascular remodeling in fibulin-4-deficient mice reveals a role of fibulin-5 in smooth muscle cell proliferation and migration", *Proc. Nat'l. Acad. Sci. U.S.A.*, 102(8):2946-2951 (2005).
Walter, et al. "Local Gene Transfer of phVEGF-2 Plasmid by Gene-Eluting Stents: An Alternative Strategy for Inhibition of Restenosis" *Circulation*, 110:36-45 (2004).
Lambert, et al., "Localized Arterial Wall Drug Delivery From a Polymer-Coated Removable Metallic Stent: Kinetics, Distribution, and Bioactivity of Forskolin" *Circulation*, 90:1003-1011 (1994).

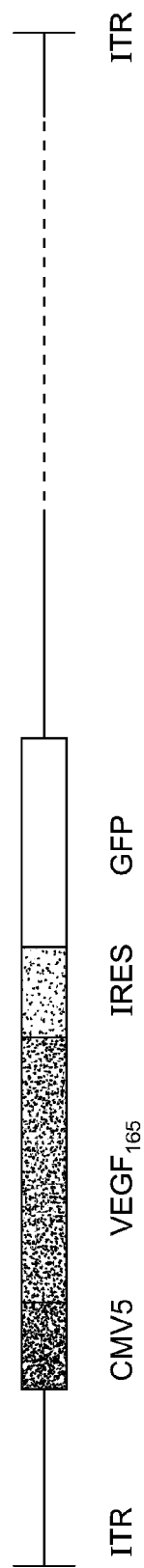 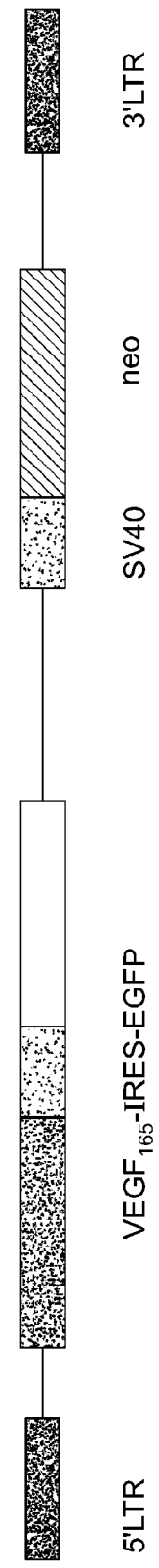
FIG. 3A
FIG. 3B

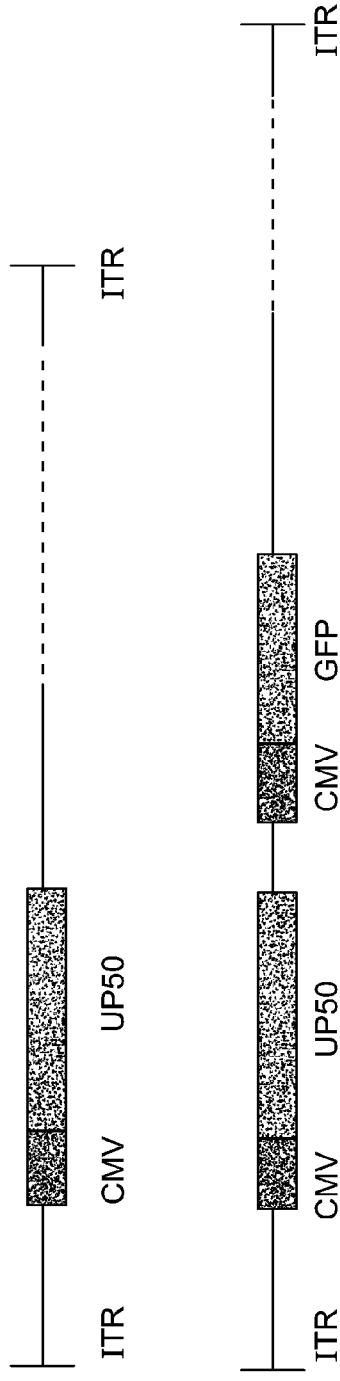
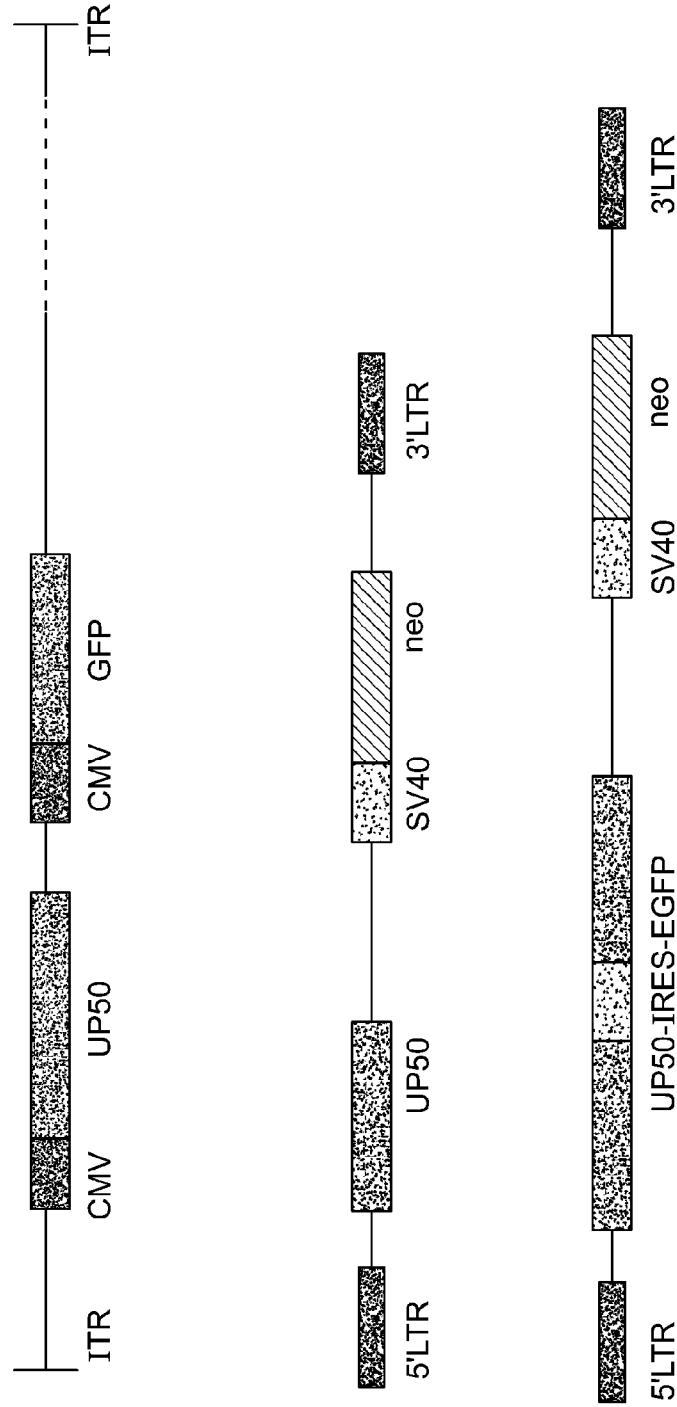
FIG. 4A
FIG. 4B
FIG. 4C
FIG. 4D

METHODS OF HEMODIALYSIS UTILIZING GRAFTS COATED WITH CELLS EXPRESSING HUMAN FIBULIN-5

RELATED APPLICATIONS

This patent application is a Divisional of U.S. patent application Ser. No. 10/164,219, filed Jun. 4, 2002, now U.S. Pat. No. 7,175,658 which is a continuation in part of U.S. patent application Ser. No. 09/620,227, filed Jul. 20, 2000 now abandoned. The contents of these applications are incorporated herein by reference in their entireties.

FIELD OF THE INVENTION

The present invention relates to the fields of chemistry, biochemistry, cellular biology, genetic engineering, medical devices and medicine. In particular, it relates to vascular grafts coated with cells genetically altered to express factors that improve the performance of the grafts.

BACKGROUND OF THE INVENTION

Vascular diseases affect a large part of the world's population. Bypass surgery, whereby a conduit, either artificial or autologous, is grafted into an existing vessel to circumvent a diseased portion of the vessel or to restore blood flow around a blocked or damaged blood vessel, is one of the most common treatments for such diseases. It is estimated that over 1 million such procedures are performed annually.

Vascular grafts are also used as entry sites in dialysis patients. The graft connects an artery to a vein in the patient's body. A needle is inserted into the graft, blood is withdrawn, passed through a hemodialysis machine and returned to the patient through a second needle inserted in the graft.

Thirty to 50 percent of bypass grafts fail within 5 to 7 years. The average life-span for hemodialysis grafts is even shorter, often less than two years.

A primary cause of graft failure is the closing of the graft due to tissue in-growth and eventually thrombosis formation. The smaller the diameter of a graft, the higher rate of failure. Numerous approaches to improving the performance of vascular grafts have been proposed. One such approach is the use of more biocompatible and durable synthetic materials in artificial grafts.

Among the synthetic materials that have been used in vascular grafts is polytetrafluoroethylene (PTFE, Teflon®), which has high durability complemented by good biocompatibility. However, PTFE and similar materials are still susceptible to thrombosis formation, which limits their utility. To counter this, the interior walls of PTFE grafts have been seeded with autologous endothelial cells (ECs) before implantation. Not only do ECs provide an excellent biocompatible surface, they also have substantial thrombolytic activity. In addition, ECs prevent neointimal proliferation and inflammatory reaction in the graft. However, EC-seeded grafts suffer from incomplete endothelialization and detachment of the endothelial cells from the surface of the graft due to the shear force of flowing blood.

To improve endothelialization, ECs have been genetically altered to express or over-express vascular endothelial growth factor (VEGF, U.S. Pat. No. 5,785,965). Not only can VEGF reduce the time from cell harvesting to seeding, it also permits use of lower initial graft seeding densities since rapid proliferation leads to faster graft coverage.

VEGF has advantages over other less EC-specific growth factors that can enhance endothelialization due to its reduced impact on other vascular cells, in particular smooth muscle cells (SMCs), and, as such, its reduced potential for causing adverse stimulatory effects. For instance, VEGF will recruit ECs, but not SMCs, from anastomosis sites.

While genetically altered ECs over-expressing VEGF resolve to a large extent the problem of incomplete endothelialization, detachment of cells from the interior surface of a graft under the shear stress of flowing blood still remains a problem.

One approach to dealing with the detachment problem has been to precoat the interior surface of a graft with an adhesive matrix to more solidly fix the cells to the surface. Also, exposing the cells seeded on the wall of the graft to continuous flow conditions during proliferation to simulate blood flow has been reported. While occurring at a slower rate, ECs still detach from the walls of grafts prepared using these techniques and thus the useful life span of the grafts remains sub-optimal. In addition, the detached cells leave extracellular matrix, which is highly thrombogenic, on the grafts after detachment.

Thus, there remains a need for endothelialized vascular grafts in which the ECs can withstand the shear force of flowing blood for a longer time. The present invention provides such vascular grafts and methods for their preparation and their use.

SUMMARY OF THE INVENTION

Thus, in one aspect, the present invention relates to an artificial vascular graft comprising a synthetic tubular element comprising a first end, a second end, an exterior surface and an interior surface that describes a lumen. A plurality of cells is seeded and cultured on the interior surface of the tubular element. The plurality of cells comprises a plurality of endothelial cells, a plurality of smooth muscle cells or a plurality of endothelial cells and a plurality of smooth muscle cells. If only endothelial cells are present, at least a portion of them is genetically altered to express or over-express one or more cell adhesion factor(s). If only smooth muscle cells are present, at least a portion of them is genetically altered to express or over-express one or more cell adhesion factor(s). If both endothelial cells and smooth muscle cells are present, at least a portion of the endothelial cells, at least a portion of the smooth muscle cells or at least a portion of both the endothelial cells and the smooth muscle cells is genetically altered to express or over-express one or more cell adhesion factor(s).

In an aspect of this invention, the cell adhesion factor is selected from the group consisting of UP50, vitronectin, albumin, elastin, tropoelastin, E-cadherins, collagen I, collagen IV, Ang-1, fibronectin and laminin.

In an aspect of this invention, the cell adhesion factor is UP50.

In an aspect of this invention, the interior surface of the tubular element comprises polytetrafluoroethylene (PTFE, Teflon™), expanded polytetrafluoroethylene (ePTFE), polyester fiber, polyethylene terephthalate (Dacron™), polyurethane, a collagen protein, an elastin protein or a processed human or animal blood vessel.

In an aspect of this invention, the interior surface of the tubular element is coated with an adhesion matrix prior to seeding with genetically altered cells.

In an aspect of this invention, the adhesion matrix is selected from the group consisting of fibronectin, collagen, elastin tropoelastin, smooth muscle cell-conditioned growth medium and any combination of thereof.

In an aspect of this invention, only a plurality of endothelial cells are present on the interior surface of the graft.

In an aspect of this invention, at least a portion of the endothelial cells are genetically altered to express or over-express one or more cell proliferation growth factor(s). In an aspect of this invention, the same endothelial cells that are genetically altered to express or over-express the cell adhesion factor(s) are also genetically altered to express or over-express the cell proliferation growth factor(s). In another aspect of this invention, the portion of the endothelial cells that is genetically altered to express or over-express the cell adhesion factor(s) is different from the portion of the cells that is genetically altered to express or over-express the cell proliferation growth factor(s).

In an aspect of this invention, the cell proliferation growth factor is selected from the group consisting of the VEGF family of proteins, acidic FGF, basic FGF and HGF.

In an aspect of this invention, when both a cell adhesion factor and a cell proliferation growth factor are present, the former is UP50 while the latter is VEGF-A.

In an aspect of this invention both a plurality of endothelial cells and a plurality of smooth muscle cells are present.

In an aspect of this invention, when both endothelial cells and smooth muscle cells are present, at least a portion of the smooth muscle cells is genetically altered to express or over-express the cell adhesion factor and at least a portion of the endothelial cells is genetically altered to express or over-express a cell proliferation growth factor.

In an aspect of this invention, when endothelial cells are present, they are cultured until a confluent monolayer is formed.

An aspect of this invention comprises smooth muscle cells, which are seeded and cultured on the exterior surface of the tubular element. In one aspect of this invention, at least a portion of the smooth muscle cells are genetically altered to express or over-express a cell adhesion factor. In another aspect of this invention, at least a portion of the smooth muscle cells are genetically altered to express or over-express a cell adhesion factor and at least a portion of the smooth muscle cells is genetically altered to express or over-express a cell proliferation growth factor. In a further aspect of this invention, the same cells that are genetically altered to express or over-express the cell adhesion factor are also genetically altered to express or over-express the cell proliferation growth factor. In a still further aspect of this invention, the portion of the cells genetically altered to express or over-express the cell adhesion factor is different from the portion of the cells genetically altered to express or over-express the cell proliferation growth factor.

In an aspect of this invention, the lumen of the artificial vascular graft has a cross-sectional area substantially equivalent to a cross-sectional area of a lumen of a vessel to which the tubular element is grafted.

In an aspect of this invention, the cross-sectional area of the lumen is from about 7 to about 700 mm$^2$.

In an aspect of this invention, the endothelial cells are obtained from a source selected from the group consisting of a vein, an artery and circulating endothelial cells. In a further aspect of this invention, the endothelial cells are derived from a source selected from bone marrow progenitor cells, peripheral blood stem cells and embryonic stem cells.

In an aspect of this invention, the smooth muscle cells are obtained from a source selected from the group consisting of a vein or an artery. In another aspect of this invention, the smooth muscle cells are derived from a source selected from bone marrow progenitor cells, peripheral blood stem cells and embryonic stem cells.

In an aspect of this invention, the endothelial cells and smooth muscle cells are obtained from a human or a non-human mammal.

In an aspect of this invention, the human from whom the cells are obtained is a patient who is to receive the vascular graft.

An aspect of this invention is a method of producing an artificial vascular graft, comprising providing a synthetic tubular element having a first end, a second end, an exterior surface and an interior surface that describes a lumen. A plurality of cells is seeded and cultured on the interior surface of the tubular element. The plurality of cells comprises a plurality of endothelial cells, a plurality of smooth muscle cells or a plurality of endothelial cells and a plurality of smooth muscle cells. If only endothelial cells are used, at least a portion of them is genetically altered to express or over-express one or more cell adhesion factor(s). If only smooth muscle cells are used, at least a portion of them is genetically altered to express or over-express one or more cell adhesion factor(s). If both endothelial cells and smooth muscle cells are used, at least a portion of the endothelial cells, at least a portion of the smooth muscle cells or at least a portion of both the endothelial cells and the smooth muscle cells is genetically altered to express or over-express one or more cell adhesion factor(s).

In an aspect of this invention, in the above method a fluidic shear force is applied at the interior surface of the tubular element during culturing of the cells.

An aspect of this invention relates to a method of bypassing a portion of a vascular vessel in a patient using an artificial vascular graft of this invention. One end of the artificial graft is grafted into the vessel proximal to the portion to be bypassed and the other end of the artificial graft is grafted into the vessel distal to the portion to be bypassed, whereby fluidic continuity is established from the site of the proximal graft, through the lumen of the tubular element, to the site of the distal graft.

A further aspect of this invention relates to a method of performing hemodialysis on a patient using an artificial vascular graft of this invention. The graft is implanted under the skin of the patient with one end of it grafted into an artery and the other end grafted into a vein whereby fluidic continuity is established from the artery through the lumen of the tubular element and into the vein. The lumen of the graft is connected to a hemodialysis filtration unit such that blood can be diverted from the lumen into the hemodialysis filtration unit, filtered, and then returned into the lumen.

DETAILED DESCRIPTION OF THE INVENTION

Brief Description of the Drawings

The drawings herein are provided solely as visual aids to the understanding the present invention. They are not intended, nor should they be construed, to limit the scope of this invention in any manner whatsoever.

FIGS. 3a-b: adenoviral (3a) and retroviral (3b) constructs that express VEGF-GFP.

FIGS. 4a-d: adenoviral vectors (4a and 4b) and retroviral vectors (4c and 4d) that express UP50 and UP50-GFP.

DISCUSSION

Figure 1:
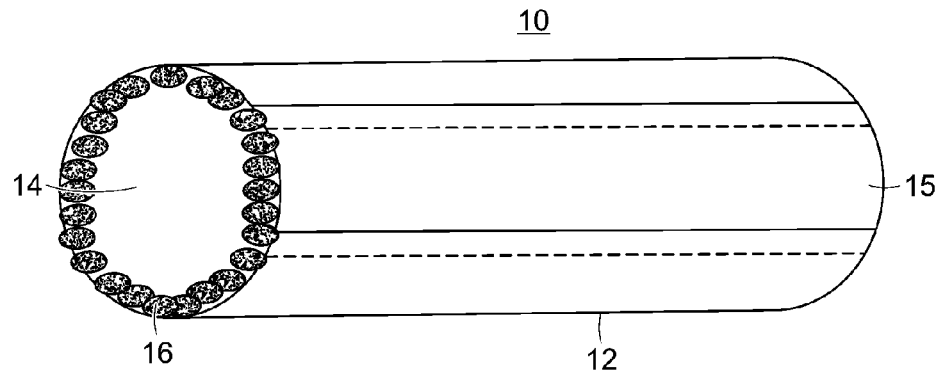
FIG. 1: a graphic representation of a vascular graft of the present invention.

Each year, numerous people lose the ability to deliver sufficient amounts of blood to various organs and limbs. The most well-known of these maladies is the coronary occlusion, the blockage of one or more of the arteries leading to the heart. However, hundreds of thousands of people also suffer loss of blood flow to the limbs. If the loss of flow is significant, tissue at the extremity becomes ischemic and eventually dies. Such loss of peripheral blood flow can result from injury but most often it is the result of disease such as atherosclerosis or diabetes complicated by accelerated atherosclerosis. To remedy these situations, surgeons often turn to vascular grafts to circumvent the injured or diseased portion of a blood vessel and restore blood flow.

Vascular grafts are generally classified as either biological or synthetic (or, synonymously, artificial). Examples of biological grafts include autografts and allografts. An autograft is taken from another site in a patient's body. For instance, in peripheral vascular surgery, the most common graft comprises the long saphenous vein in which the valves have been surgically removed with an intraluminal cutting valvutome.

An allograft, on the other hand, is a biological graft taken from another animal or the same or different species.

Synthetic or artificial grafts are made of non-biological materials such as, without limitation, polytetrafluoroethylene (PTFE Teflon®), expanded PTFE (ePTFE), polyester, polyurethane, polyethylene terephthalate (Dacron®) and the like. Dacron grafts are commonly used in aortic and aorto-iliac surgery. Presently, below the inguinal ligament, results with synthetic grafts are considered inferior to biological (venous) grafts. However, when a suitable vein is not available, PTFE is most often the graft material of choice. Also, using a synthetic graft results in a shorter operation and spares veins for future procedures.

Artificial grafts are not yet used extensively in heart bypass procedures. One of the limitations of these grafts (and some biological grafts as well) is the lack of long-term patency, that is, the ability to remain open to blood flow for extended periods. This is particularly problematic with regard to small blood vessels such as those related to below inguinal peripheral blood vessels and the coronary arteries. While large and medium diameter blood vessel replacement with a Dacron® or Teflon® graft may have a patency of 10 year or more, the results with small blood vessels have been markedly poorer. The problem is that the lumens of these grafts tend to occlude due to tissue in-growth and thrombosis, i.e., formation of blood clots. Endothelial cells (ECs) are sometimes used to line the lumen of synthetic grafts. The cells enhance performance of the grafts due to their thrombolytic activity (Dichek, et al., *Circulation,* 1996, 93:301; Gillis-Haegerstrand, et al., *J. Vasc. Surg.,* 1996, 24:226) and their ability to prevent neointimal proliferation (tissue and extracellular in-growth) and inflammatory reactions in the graft (Pasic, et al., *Circulation,* 1995, 92:2605). Unfortunately, the cells often cannot withstand the shear force of flowing blood and eventually detach from the surface of the graft, thus negating their utility. The synthetic vascular grafts of this invention address this situation.

A graft of this invention comprises a tubular element manufactured from a completely synthetic material such as, without limitation, PTFE (Teflon®), ePTFE, polyethylene terephthalate (Dacron®), polyester or polyurethane. While rigid-walled grafts may be used in the circulatory system, they are not preferred due to their tendency to detrimentally effect blood wave propagation and local field velocity, thus acting in essence as "low pass filters" that damp out higher harmonics and introduce phase distortion. Thus, artificial grafts are most often manufactured in a textile motif, that is, they are usually fibrous materials that are woven or knitted although polyurethane grafts may be extruded.

A "synthetic" graft of this invention may also comprise a processed animal or human blood vessel.

A typical synthetic graft of this invention is shown in FIG. 1. Graft 10 is comprised of a synthetic tubular element 12 having an outer surface 20 and an interior surface 14 that describes a lumen 13. Synthetic tubular element 12 has an inner cross-sectional area that is substantially equivalent to the inner cross-sectional area of the vessel to which it is grafted. In a presently preferred embodiment of this invention, the inner cross-sectional area is about 7 to 700 mm$^2$. Interior surface 14 is constructed of a material such as, without limitation, PTFE, ePTFE, polyester fiber, collage fiber, elastin fibers, polyurethane, Dacron® or processed blood vessels obtained from an animal or human. Interior surface 14 preferably has a structure that facilitates cell seeding such as, without limitation, pits and/or projections.

In a presently preferred embodiment of this invention, interior surface 14 is coated with ECs and/or SMCs 16, at least a portion of which are genetically altered to express one or more cell proliferation growth factor(s) and a portion of which are altered to express one or more cell adhesion factor (s).

Cell proliferation growth factors include HGF (hepatocyte growth factor), EGF (epidermal growth factor), Epo (erythropoietin), FGFs (fibroblast growth factors), IGF (insulin-like growth factor), IL (interleukins), platelet derived growth factor (PDGF), transforming growth factor (TGF) and vascular endothelial growth factor (VEGF). While any of these may be used in the devices and methods of this invention, VEGF, which is a member of the PDGF family, is presently preferred because it is a very specific stimulator of the vascular endothelium.

The VEGF family at present consists of VEGF-A, VEGF-B, VEGF-C, VEGF-D and the most recently discovered VEGF-E. PIGF (placenta growth factor) is closely related to VEGF-A and is often considered a pseudo-VEGF family factor. Any of these may be, in fact, are presently preferred to be, used in the grafts and methods of this invention.

Cell adhesion factors useful in the grafts and methods of this invention include, without limitation, those factors that are considered part of the extracellular matrix (ECM) that connect the cell membrane to the ECM.

In a presently preferred embodiment of this invention, interior surface 14 is coated with ECs and/or SMCs, wherein the same cells are genetically altered to express both a cell proliferation growth factor and a cell adhesion factor.

In addition, external surface 15 of tubular element 12 can be coated with altered or unaltered smooth muscle cells to improve graft acceptance as well as to aid in graft durability.

Endothelial cells (ECs) are those cells that cover the interior or luminal surface of blood vessels. They serve numerous purposes, one of the most important of which with regard to the present invention is the prevention of thrombosis, i.e., blood clot formation, in the vessel as well as prevention of tissue in-growth and undesirable production of extracellular matrix. ECs useful in the synthetic grafts of this invention include, without limitation, arterial and venous ECs such as human coronary artery endothelial cells (HCAEC), human aortic endothelial cells (HAAEC), human pulmonary artery endothelial cells (HPAEC), dermal microvascular endothelial cells (DMEC), human umbilical vein endothelial cells (HUVEC), human umbilical artery endothelial cells (HUAEC), human saphenous vein endothelial cells (HSVEC), human jugular vein endothelial cells (HJVEC), human radial artery endothelial cells (HRAEC), and human internal mammary artery endothelial cells (HIMAEC). Useful ECs can also be obtained from circulating endothelial cells and endothelial cell precursors such as bone marrow progenitor cells, peripheral blood stem cells and embryonic stem cells.

Smooth muscle cells encircle the endothelial cells in a vessel and regulate the vessel's diameter by expanding and contracting. Most importantly for the purposes of this invention, smooth muscle cells are responsible for the secretion of most of the extracellular matrix. Smooth muscle cells useful in the grafts of this invention include, without limitation, human aortic smooth muscle cells (HAMC), human umbilical artery smooth muscle cells (HUASMC), human pulmonary artery smooth muscle cells (HPASMC), human coronary artery smooth muscle cells (HCASMC), human bronchial smooth muscle cells (HBSMC), human radial artery smooth muscle cells (HRASMC), and human saphenous or jugular vein smooth muscle cells.

The extracellular matrix (ECM) is a complex material that surrounds and supports cells in mammalian tissue. It is commonly referred to as the connective tissue. The ECM is composed of three major classes of biomolecules: structural proteins (collagen, elastin), specialized proteins (fibrillin, fibronectin, laminin) and proteoglycans (protein cores to which are attached repeating disaccharides called glycosaminoglycans).

Collagens comprise the major proteins of the ECM. In fact, they are the most abundant proteins found in the animal kingdom. There are at least 20 types of collagen. Collagen types I II and III are the most abundant and form fibrils of similar structure. Type IV forms a two-dimensional reticulum and is a major component of the basal lamina. Collagens are predominantly synthesized by fibroblasts in the natural state although epithelial cells also synthesize some collagen.

Fibronectin's role in the ECM is to attach cells to a variety of extracellular matrices. For example, fibronectin has been shown to attach cells to collagen I-, II- and III-containing ECMs.

Fibronectin does not attach cells to collagen IV-containing ECMs. In this case, laminin is the adhesive molecule.

Other cell adhesion factors include elastin and its precursor tropoelastin. Elastin is extremely insoluble due to extensive cross-linking of tropoelastin, which prior to cross-linking is quite soluble. Elastin and tropoelastin, are synthesized naturally by both smooth muscle and endothelial cells.

Endothelial cadherins (E-cadherins) are calcium dependent adhesion molecules. They tend to bind in a homophilic manner, that is, one cadherin binds to another cadherin in the extracellular space. The connections occur at specialized junctions.

Vitronectin, also known as S-protein, serum spreading factor and epibolin, is present in the extracellular matrix of many tissues. Along with fibronectin it is the major adhesive protein in plasma and serum. Interaction of vitronectin with other ECM components is mediated primarily by its collagen-binding domain. Used as a pre-coating on surfaces, vitronectin promotes cell attachment, spreading, proliferation and differentiation of many different types of cells.

The recently discovered protein, UP50, also know as fibulin 5 or DANCE (Developing Arteries and Neural Crest, EFG-like), has also been found in the ECM. UP50 has been implicated in the generation and organization of elastic fibers, which are essential to various organs that require elasticity, such as the lungs, large arteries and skin. This protein has an RGD motif that interacts with cell surface integrins and promote cell to matrix adhesion.

Many of the above factors are naturally expressed by ECs and SMCs. These cells can be genetically altered to overexpress the factors to improve the performance of the cells as coatings on the interior surface of artificial grafts, in particular with regard to resistance to shear stress. If, on the other hand, a desired factor is not naturally expressed, the cells can likewise be genetically altered to express it.

While expression of cellular adherence factor(s) by the seeded cells themselves results in substantially improved cell-to-cell and cell-to-graft adhesion, it is also an aspect of this invention to pre-coat the interior surface of a graft with one or more ECM proteins such as, without limitation, fibronectin, prior to seeding with genetically altered ECs or SMCs to enhance adhesion even more. The proteins can be harvested from the cell cultures used to initially grow the ECs and SMCs, or can be isolated from the blood. It is also an aspect of this invention to use the cell culture medium itself after culturing of the cells, in which case the medium is termed a "conditioned medium." A presently preferred conditioned medium is that obtained from cultures of altered or unaltered SMCs.

The above cells are genetically altered such that a portion of them express one or more cellular proliferation growth factors and a portion of them express one or more of the above ECM cellular adhesion factors. It is, however, a presently preferred embodiment of this invention that the same cells are genetically altered to express both a cellular proliferation factor and a cellular adhesion factor.

In a presently preferred embodiment of this invention the above, cells are seeded onto the interior surface of the graft and cultured to confluence.

It is noteworthy that improved adhesion conferred by the expression of a cellular adhesion factor does not come at the expense of cell proliferation, which has been found to proceed normally.

Figure 2:
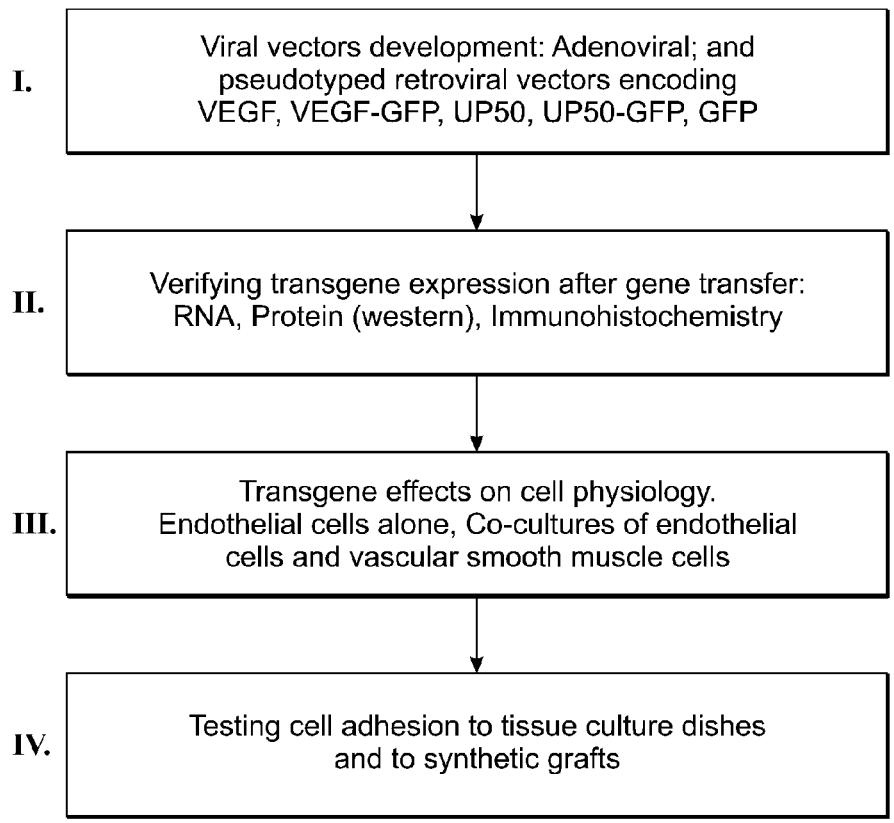
FIG. 2: a flowchart of the strategy for constructing a hybrid biological-synthetic vascular grafts of the present invention.

FIG. 2 is a flow chart that lays out the experimental design used to prepare and evaluate the artificial grafts of this invention.

First, vectors must be developed that reliably transfect cells to express a proliferation growth factor, an adhesion factor or both. In the present case, either one of two types of viral vectors was employed to transfer genes into vascular cells. The first was a recombinant adenoviral vector that gave high levels of transgene expression. Such vectors have the advantage of being less difficult to prepare than adeno-associated vectors (AAV) and lentiviral-based vectors. Furthermore, unlike other viral vector systems, adenoviral vectors may be employed after cell seeding of grafts because cell division is not essential for transgene expression. In contrast, retroviral vectors requires cell division, which, in the present invention, is generally carried out to a great extent on the tissue culture plate and less so on the graft.

The second vector was a retroviral vector pseudo-typed with GALV (Gibbon ape leukemia virus glycoprotein. Pseudo-typed vectors have a high affinity for human ECs and SMCs (Cosset, F.-L. and Russell, S. J., *Gene Therapy*, 1996, 3:946-56) and, unlike adenoviral vectors, transduction with retroviral vectors leads to stable transgene expression and transmission of gene expression in daughter cells and to less immunogenic reaction in vivo.

The vectors listed in Table 1 were used to transfer UP50 and VEGF$_{165}$ genes into ECs and SMCs. FIGS. 3a, 4a and 4b depict the adenoviral VEGF$_{165}$-GFP, UP50 and UP50-GFP expression vectors and FIGS. 3b, 4c and 4d depict the retroviral VEGF$_{165}$-GFP, UP50 and UP50-GFP vectors used.

TABLE 1

| Viral system | Packaging cell line | Gene(s) Encoded | Designation | Titer |
|---|---|---|---|---|
| Adenovirus | | GFP | Ad.GFP | $10^{10}$ pfu/ml |
| Adenovirus | | VEGF-IRES-GFP | Ad.VEGF-GFP | $10^{10}$ pfu/ml |
| Adenovirus | | UP50-GFP | Ad.UP50-GFP | $5 \times 10^{10}$ pfu/ml |
| Adenovirus | | UP50 | Ad.UP50 | pending |
| Pseudo-typed Retrovirus | TEFLYGA | GFP | RetroGFP | $10^6$ ffu |
| Pseudo-typed Retrovirus | TEFLYGA | VEGF-IRES-GFP | RetroVEGF-GFP | $5 \times 10^5$ ffu |
| Pseudo-typed Retrovirus | 293FLYGA | UP50-IRES-GPF | RetroUP50-GFP | $10^6$ ffu |
| Pseudotyped Retrovirus | 293FLY10A | UP50-IRES-GPF | RetroUP50-GFP | $10^6$ ffu |
| Pseudo-typed Retrovirus | 293FLYGA | UP50 | RetroUP50 | $10^6$ ffu | ePTFE grafts seeded with human ECs transfected with Ad.UP50-GFP were found to express GFP as observed by fluorescent microscopy. ePTFE grafts seeded with human ECs transfected with Ad.VEGF-GFP were likewise found to express the transgene. Transgene expression was analyzed 24 hours following infection.

ePTFE grafts seeded with retrovirally-transduced human ECs over-expressing UP50-GFP, were found to express the transgene, also by fluorescent microscopy detection of GFP expressing cells since the UP50 is situated upstream in the expression cassette (if GFP is expressed UP50 must be expressed). Grafts seeded with retrovirally-transduced human ECs over-expressing VEGF-GFP were similarly found to express the transgene. Transgene expression was analyzed 48 hours following seeding.

Human EC identity was verified by immunohistochemical staining for CD31 (PECAM).

Transfection of ECs and SMCs by recombinant adenovirus encoding UP50-GFP also resulted in transgene expression. Transduction of ECs and SMCs by retroviral vector encoding UP50-GFP similarly resulted in production of GFP.

Transcription of UP50 mRNA was detected by RT-PCR analysis of Ad.UP50-GFP transfected ECs and SMCs and in ECs and SMCs genetically altered with retroviral vector encoding UP50-GFP.

UP50 (60 kD) expression was detected by Western blot analysis following transfection of ECs and SMCs with adenoviral and transduction with retroviral vectors encoding UP50-GFP.

UP50 was detected in Ad.UP50-transfected ECs and SMCs, by immunohistochemical analysis. Cytoplasmic staining occurred in Ad.UP50-GFP transfected cells but not in Ad.GFP transfected cells, indicating high level cytoplasmic expression of UP50.

Confocal microscopy was used to determine the sub-cellular location of UP50 within transfected ECs. UP50 was detected in Ad.UP50-GFP transfected endothelial cells in both the cytoplasm and in the cell membrane. It was also detected as filamentous structures in confluent cells.

The presence of UP50 in the ECM was detected by immunohistochemical analysis of ECs transfected with an adenoviral vector encoding UP50-GFP.

Co-cultures of ECs and/or SMCs, a portion of which were transfected with Ad.VEGF-GFP and a portion of which were transfected with Ad.UP50-GFP were found to express significant levels of VEGF and UP50. Likewise, analysis of co-cultures of SMCs and ECs, a portion of which were retrovirally transduced to express UP50 and a portion of which were retrovirally transduced to express VEGF were found to co-express significant levels of the factors by Western blot analysis.

Figure 5:
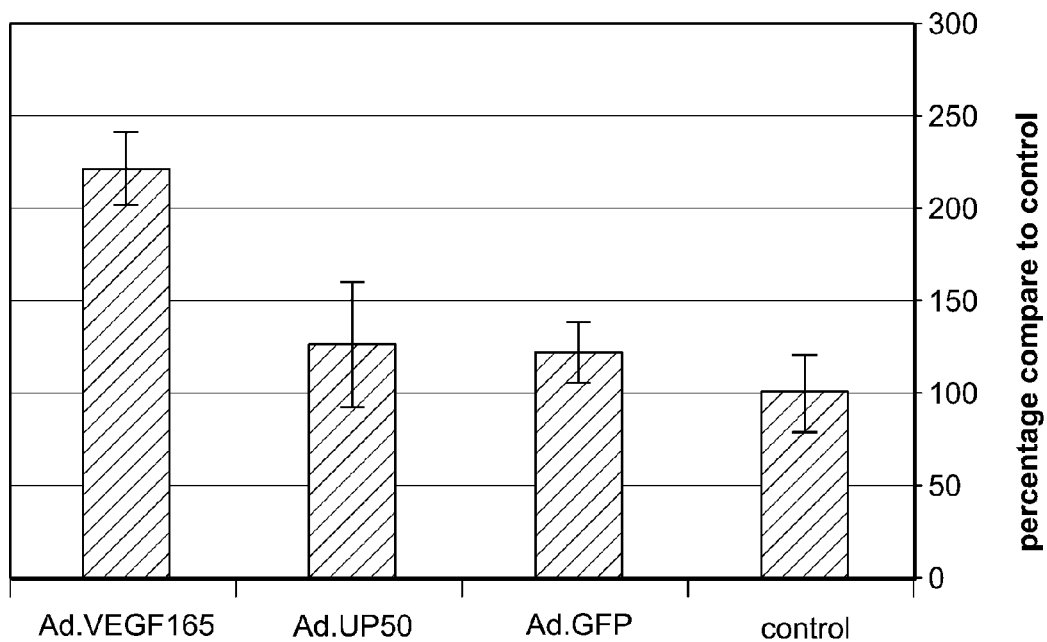
FIG. 5: histogram showing the proliferation of ECs transfected with adenoviral vectors encoding UP50-GFP, VEGF-GFP or GFP.
Figure 6:
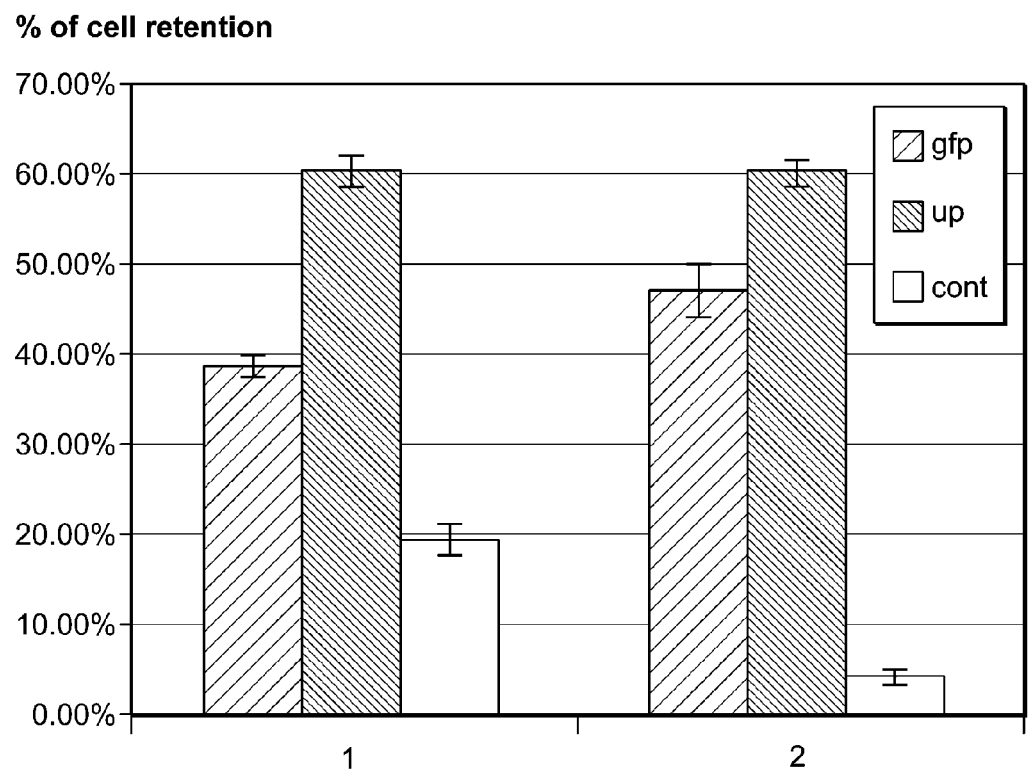
FIG. 6: histogram derived from an adhesion assay of Ad.UP50 transfected ("UP legend), Ad.GFP transfected ("gfp" legend) or non-transfected ("cont" (control) legend) ECs. Two different experiments, performed in triplicate, are represented.

The above infections/transductions produced almost 100% transgene-expressing cells, as detected by cytoplasmic GFP expression. Transgene over-expression of UP50 had no inhibitory effect on cell growth and proliferation (FIG. 5). Although the values measured in the adenovirus-transfected cells (Ad.GFP, Ad.UP50-GFP) were slightly higher than the non-infected control group, the effect of UP50 expression was not significant. There was no significant difference between ECs transfected with Ad.GFP and ECs transfected with Ad.UP50-GFP. Transfection with Ad.VEGF$_{165}$-GFP induced significant proliferation compared to other factors.

The above demonstrates the viability of using co-cultures of cells some of which express a proliferation growth factor and some of which express a cell adherence factor. It is, however, a presently preferred embodiment of this invention to have the same cells express both factors. Therefore, ECs transduced with retroviral vector encoding UP50-GFP or GFP were incubated for 48 hrs and then infected with Ad.VEGF-GFP or Ad.GFP. The cells were incubated for an additional 24 hours in virus-containing medium. The virus medium was then replaced with serum-free medium and the cells were incubated for an additional 24 hours. Samples of the growth medium (30 μl) were separated on 10% SDS polyacrylamide gel, electroblotted onto a nitrocellulose membrane and incubated with either anti-VEGF or anti-UP50 antibody. Following exposure to a peroxidase-conjugated secondary antibody, the blots were developed with ECL reagents and exposed to X-ray film. The ECs retrovirally transduced to express UP50-GFP and subsequently transfected with adenoviral vector encoding VEGF-GFP displayed higher levels of GFP expression than cells infected with retroviral vector encoding UP50-GFP only, as determined by fluorescence microscopy. Western blot analysis further confirmed that the cells co-expressed VEGF and UP50 protein. Next, the use of ECs genetically altered to express both mitogeic and adhesion factors to produce synthetic vascular grafts possessing long-term biocompatibility and patency was investigated.

Human saphenous vein ECs were retrovirally transduced with two separate viral vectors, VEGF-GFP and UP50-GFP. Following transduction, the cells were seeded on ePTFE grafts. Fluorescence microscopy was used to view endothelial cells in a cell culture dish after being transduced first with a retroviral vector encoding UP50-GFP and, 72-96 hours later, with a retroviral vector encoding VEGF-GFP to demonstrate that cells can survive dual gene transduction and maintain normal morphology. A Western blot was used to show that twice-transduced cells in fact express both genes. That is, in the blot, a dense band in the upper portion indicated that UP-50 is being over-expressed while a dense band in the lower region indicates that VEGF is being over-expressed.

To regulate the expression of transgene in ECs, an effector-regulated expression system may be used. For example VEGF expression can be up-regulated and UP50 expression down-regulated by using promoters that are themselves up-regulated and down-regulated by tetracycline. In this manner, cells can be made to express or over-express a cell adhesion factor, e.g., UP50, in the first week following bypass surgery when cell adhesion is a priority. Then, tetracycline can be administered to down-regulate the cellular adhesion factor expression while simultaneously up-regulating expression of a cell proliferation factor, e.g., VEGF, to effect enhanced coverage of the graft.

Alternatively, cells can be retrovirally transduced to stably express or over-express UP50 and then transfected with Ad.VEGF in such a manner that expression of VEGF is transient. (Example 12).

Transgene expression having been verified, the effect of expression on cell physiology was next investigated. To accomplish this, in vitro angiogenesis in collagen gels was examined using adenovirus-infected EC spheroids. The generation of spheroids is described in the Examples section. The spheroids of Ad.GFP or AdUP50-GFP transfected ECs were found to have a low baseline sprouting activity. Sprouting was strongly stimulated by addition of exogenous VEGF to either. Likewise, spheroids of Ad.GFP or Ad.UP50-GFP transfected ECs showed a low baseline sprouting activity. Sprouting activity was stimulated in 50% co-cultures with Ad.VEGF-GFP infected ECs. The highest sprouting levels were observed in a co-culture of Ad.UP50-GFP and Ad.VEGF-GFP transfected ECs.

In a different set of experiments, which examined cell adhesion (i.e., retention), expression of UP50 following recombinant adenoviral transfection was shown to significantly increase cell retention (60%) compared to Ad.GFP infected cells (40%) or control, non-transfected cells (20%). It can be concluded, therefore, that co-over-expression of UP50 with VEGF increases sprouting of EC compared to that mediated by VEGF alone. These results demonstrate that ECs expressing such a combination of factors exhibit an enhanced proliferative and adhesive capacity.

In a presently preferred embodiment of this invention, the proliferation growth factor is VEGF (GenBank Accession Number AB021221), acidic or basic FGF (GenBank Accession Numbers S67291 and M27968) or HGF (GenBank Accession Number D14012).

In a presently preferred embodiment if this invention, the cellular adherence factor is UP50 (SEQ ID NO. 1), fibulin-5/DANCE (GenBank Accession Number AF112152), vitronectin (GenBank Accession Number NM000638), albumin (GenBank Accession Number NM000477), collagen I (GenBank Accession Number J00114), collagen IV (GenBank Accession Number M15524), fibronectin (GenBank Accession Number X02761), laminin (GenBank Accession Number NM005560), tropoelastin (GenBank Accession Number XM065759, or VE cadherin (GeneBank Accession Number NM001795).

Other cellular adhesion factors that ECs or SMCs can be engineered to express or over-express will become apparent to those skilled in the art based on the disclosure herein. All such adhesion factors are within the scope of this invention.

Preferably, when both ECs and SMCs are used, the cell proliferation growth factor promotes the proliferation specifically of the ECs so as to avoid unwanted proliferation of SMCs. That is, SMCs are desirable where they can assist in providing a better surface for the adherence of the endothelial cells, which is the manner in which they are employed in the present invention. Thus, the use of SMCs on the exterior (abluminal) surface of a graft of this invention can result in the migration of extracellular matrix produced by the SMCs through the graft and onto the interior surface where the matrix will provide an improved surface for the ECs. Likewise, the use of SMCs on the interior surface of the graft is intended to produce a monolayer of SMCs on the interior surface to mimic the structure of vascular vessels in which such a layer naturally occurs beneath the layer of ECs.

To produce graft 10, cells 16 are seeded, that is, multiple cells or colonies of endothelial cells are placed on interior surface 14 of element 12 and then the cells are cultured so that they will adhere and, when needed, will grow and proliferate until a sufficient degree of coating of interior surface 14 is achieved. Preferably, cells 16 are cultured under conditions that result in a confluent monolayer of cells on interior surface 14. By a "confluent monolayer" is meant the stage in the proliferation of the endothelial cells at which they all come in contact with each other to form a continuous, uniform coating on the surface. At this point, normal cells stop proliferating due the phenomenon of contact inhibition.

Prior to seeding the interior surface may be coated with substances that aid in the adhesion, growth and proliferation of the endothelial cells. These substances may include, without limitation, amino acids, nucleotides, serum proteins, salts, vitamins, a supplemental serum such as human serum (FCS). Exogenous ECM substances may also be included to enhance adhesion of the cells to the surface.

Several seeding approaches can be used to coat interior surface 14 of graft 10. When both ECs and SMSc are used, the cells may be seeded simultaneously or sequentially on interior surface 14. Sequential seeding, first SMCs, then ECs, is presently preferred. That is, altered or unaltered SMCs are preferably seeded first followed by seeding with altered ECs. This predisposes the cells to their normal position, that is, SMCs beneath and between the ECs and the interior surface of the graft. When simultaneous seeding is employed, the cells may migrate to their desired locations that is the SMCs migrate toward the surface of the graft and the ECs migrate so as to be on top of the SMCs. When sequential seeding is employed the time between seeding can vary but the presently preferred time lapse between seeding with SMCs and seeding with ECs is 24-96 hours. Since it is known that ECs have a natural affinity for SMCs, it is possible to seed a graft with SMCs, preferably genetically altered to over-express an adhesion factor to enhance the effect even more, and then allow seeded or circulating endothelial cells to adhere to the SMCs.

Cells 16 can be altered so that the same cells express both the cell proliferating growth factor and the cellular adhesion factor. In the alternative, one portion of the cells can be altered to express the cell proliferating growth factor and another portion can be altered to express the cellular adhesion factor. In general, when different cells are used to express or over-express a cell proliferation growth factor and an adhesion factor, it is preferred that a greater proportion of cells that express or over-express the cell adhesion factor are used. It is presently preferred that from about 60% to about 90% of the cells express or over-express the cell adhesion factor. Most preferred are cells that express or over-express both a cell proliferation growth factor and a cell adhesion factor, in which case, of course, the proportion is 1:1. Such cells were found to adhere better to a graft that native cells or cells expressing or over-expressing VEGF or UP50 alone.

ECs and SMCs can be obtained from various mammalian tissue sources. For example, ECs can be obtained from, without limitation, a segment of a vein, a segment of an artery, bone marrow progenitor cells, peripheral blood stem cells, embryonic stem cells or circulating endothelial cells. Smooth muscle cells can be obtained from, without limitation, human saphenous veins, left internal mammary arteries, the radial artery, bone marrow progenitor cells, embryonic stem cells, and peripheral blood stem cells.

In a presently preferred embodiment of this invention, ECs and SMCs are obtained from tissues of the intended recipient of the graft or a syngeneic donor.

Of course, it is possible to obtain ECs and SMCs that can be used in the devices and methods of this invention from xenogeneic tissue providing measures are taken to avoid cell rejection. These measures include, without limitation, use of transgenic animal tissues that express the human decay accelerating factor or that do not express the a-Gal epitope. Also, well-known immune suppressive drugs are often used. These and numerous other methods for reducing the risk of rejection are well-known in the art. Those skilled in the art will know which of these techniques would be best employed in a given situation. All such measures are within the scope of this invention.

The proliferation and adhesion factors can be encoded by polynucleotide sequences derived from human or other mammalian cells provided the factors expressed by the sequences are functional in ECs and SMCs.

The proliferation and adhesion factors can be endogenous or xenogenous to the EC or SMC cells used. If they are endogenous, that is if some or all of them are already expressed by the cells, the cells can be genetically altered to over-express one or more or of them. The cells can also be genetically altered to express desirable xenogenous factors.

As used herein, the terms "over-express," "over-expressed," or "over-expression" refer to expression levels that exceed those normally produced by a cell. Over-expression can be induced by introducing additional copies of an endogenous gene into a cell, which results in a higher level of expression of the factor. Over-expression can also be induced by introducing enhancer sequences into the cellular genetic material that up-regulate the transcription or translation of the endogenous genes. The latter can be accomplished by, for example, gene "knock-in" techniques, which are well-known in the art. It also can be achieved by introducing factors that will reduce level of RNA degradation or that will stabilize RNA of the relevant gene. These and other procedures that result in over-expression of genes and that will be useful with regard to the present invention will become apparent to those skilled in the art based on the disclosures herein. All such techniques are within the scope of this invention.

As used herein the phrase "genetically alter" refers to the introduction of one or more exogenous polynucleotide sequences into a cell. The sequences may be duplicates of sequences already in the cell's genetic material as might be the case where over-expression is the goal. Or, the sequences may be entirely xenogenous, such as would be the case of the cell does not normally express the factor encoded by the sequence. The sequences may integrate into the genome of the cell, thus becoming a permanent part thereof, or they may remain as separate, transient entities in the nucleus or cytoplasm of the cell. As described elsewhere herein, both stable and transitory expression of factors may, under certain circumstances be useful in carrying out the methods of this invention.

Another aspect of the present invention is a nucleic acid expression construct for genetically altering ECs and SMCs for use in the methods herein. As used herein, a "nucleic acid construct" refers to one or more polynucleotide sequences that encode for one or more of proliferation and/or adhesion factors. In a presently preferred embodiment, the construct comprises two sequences, one that encodes a cell proliferation growth factor and one that encodes a cell adhesion factor. A "polynucleotide sequence" refers to a linear array of nucleotide residues that encodes the expression of a particular factor. In a presently preferred embodiment, the construct also comprises one or more promoter sequences for directing the expression of the polynucleotide sequences. A promoter is a DNA sequence that facilitates the binding of RNA polymerase to a template and initiates replication. A promoter initiates transcription only of the gene or genes physically connected to it on the same stretch of DNA, that is, the promoter must be "in cis" with the gene it affects. A promoter may be constitutive, that is, always "on" and capable of initiating transcription at any time. It may be tissue specific and only initiate transcription in certain tissue environs. Or it may be inducible, in which case another molecule, known as an effector, or some other external influence such as, without limitation, temperature, light, shear stress, pH, pressure, etc., is needed to "induce" the promoter to operate. Any of these types of promoters may be used in the constructs of this invention and are within its scope.

As is further described in the Examples section, the cell proliferating growth factor and the cellular adherence factor may be expressed in different temporal patterns. That is, if desired, the expression of the genes can be controlled such that expression or over-expression of the cell adhesion factor can occur first and then, at a later time, expression or over-expression of the cell proliferation growth factor can be up-regulated. If desired, expression of the cell adhesion factor can be down-regulated when expression of the cell proliferation growth factor is up-regulated. However, it is presently preferred that expression or over-expression of the cell adhesion factor is simply maintained when the expression or over-expression of the cell proliferation growth factor is up-regulated.

In a presently preferred embodiment, the nucleic acid expression construct comprises two promoter sequences, each directing the expression of one of the polynucleotide sequences. It is further presently preferred that the promoters be inducible and that they are regulated by the same effector molecule. It is also presently preferred that the promoter sequences are selected such that one promoter is up-regulated and, at the same time, the other promoter is down-regulated by the effector.

Suitable inducible promoters include, without limitation, chemically (effector) induced promoters such as those used in the Tet-On™ and Tet-Off™ gene expression systems commercially available from Clontech. Another example is shear stress induced promoters.

In the alternative, a single promoter sequence can be used to regulate both polynucleotide sequences provided that they are transcriptionally linked and that an internal ribosome entry site (IRES) is included for directing the translation of the second sequence of the polycistronic message.

The two polynucleotide sequences can also be translationally fused provided a protease cleavage site is inserted between the sequences so that cleavage and separation of the two polypeptides can occur in expressing cells.

If desired, the two polynucleotide sequences can be provided as separate nucleic acid constructs that are co-introduced into the cells.

Another aspect of the present invention is a nucleic acid construct system for genetically altering cells of this invention. A construct system, as the term is used herein, comprises two nucleic acid expression constructs as described above. One would encode for the cell proliferating growth factor and the other for the cellular adherence factor.

In a presently preferred embodiment, the expression construct or construct system includes additional polynucleotide sequences that code for reporter markers, selection markers and the like. Selection markers are used to assist in determining which cells have been genetically altered cells and isolating those cells. A common selection marker is antibiotic resistance. That is, a resistance gene is inserted into the cell along with the desired factor gene. After the cells have been treated with a vector, those that were successfully infected will survive exposure to an antibiotic and can be isolated while those that were not infected will die. Reporter markers are used to monitor the expression of cell proliferating growth factor(s) and cellular adherence factor(s). Examples of reporter markers include, without limitation, beta-galactosidase, luciferase and green fluorescent protein (GFP). Other selection and reporter markers that would be useful in the production of the genetically altered cells herein will become apparent to those skilled in the art based on the disclosures herein and are within the scope of this invention.

To monitor expression of the cell proliferation growth factor and the cellular adherence factor, the reporter marker gene can be transcriptionally linked or translationally fused to the polynucleotide sequence encoding the factor. Or, it can be placed under the transcriptional control of a promoter sequence identical to that directing the transcription of the factor.

The polynucleotide sequences encoding the cell proliferating growth factor and the cellular adherence factor can be ligated into a commercially available expression vector system suitable for transforming mammalian cells and for directing the expression of the factors in the cells. Such commercial vector systems can easily be modified by recombinant techniques well known in the art to replace, duplicate or mutate existing promoter or enhancer sequences or to introduce additional polynucleotide sequences.

Suitable mammalian expression vectors include, without limitation, pcDNA3, pcDNA3.1(+/−), pZeoSV2(+/−), pSecTag2, pDisplay, pEF/myc/cyto, pCMV/myc/cyto, pCR3.1 (Invitrogen); pCI (Promega); pBK-RSV and pBK-CMV (Stratagene) and pTRES (Clontech), and derivatives thereof.

A nucleic acid expression construct or construct system useful herein to up-regulate a factor may comprise transcriptional regulatory sequences in cis to endogenous sequences encoding the cell proliferation growth factor or the cellular adherence factor. By "in cis" is meant that the regulatory sequence is on the same DNA molecule as the sequence it is regulating. Alternatively, an expression construct or construct system useful to up-regulate a factor may comprise translational regulatory sequences in trans to endogenous sequences encoding the cell proliferating growth factor or the cellular adherence factor. By "in trans" is meant that the regulatory sequence is present on a different molecule of DNA than the sequence it is regulating.

Gene "knock-in" techniques well-known in the art can be used to introduce cis acting transcriptional regulatory sequences into the genome of the Ecs or SMCs (U.S. Pat. Nos. 5,487,992, 5,464,764, 5,387,742, 5,360,735, 5,347,075, 5,298,422, 5,288,846, 5,221,778, 5,175,385, 5,175,384, 5,175,383 and 4,736,866, each of which is incorporated by reference, including any drawings, as if fully set forth herein. See also, International publications WO 94/23049, WO93/14200, WO 94/06908 and WO 94/28123. For additional general information on the technique, see Burke and Olson, Methods in Enzymology, 194:251-270, 1991; Capecchi, Science 244:1288-1292, 1989; Davies et al., Nucleic Acids Research, 20 (11) 2693-2698, 1992; Dickinson et al., Human Molecular Genetics, 2(8):1299-1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991; Jakobovits et al., Nature, 362:255-261 1993; Lamb et al., Nature Genetics, 5: 22-29, 1993; Pearson and Choi, Proc. Natl. Acad. Sci. USA, 1993, 90:10578-82; Rothstein, Methods in Enzymology, 194:281-301, 1991; Schedl et al., Nature, 362: 258-261, 1993 and Strauss et al., Science, 259:1904-1907, 1993.

The nucleic acid expression constructs of the present invention can be introduced into ECs and SMCs using any of a number of methods including, but not limited to, direct microinjection of DNA, protoplast fusion, diethylaminoethyldextran and calcium phosphate-mediated transfection, electroporation, lipofection, adenoviral transfection, retroviral transduction and others. Such methods are well-known in the art and any of them are within the scope of this invention.

To assess the stability and adhesion of vascular ECs and SMCs to an ePTFE graft in vivo, an artificial pulsatile flow device, which can simulate a variety of mechanical and hemodynamic forces resembling in vivo conditions was developed. The device can also be used for quality assurance prior to implanting a biosynthetic product.

The device comprises a pulsatile blood pump. (Harvard apparatus #1421, USA), rigid stainless steel 316L tubes (OD of 12 mm and 6 mm), flexible Teflon tubes (OD of 12 mm and 6 mm), stainless steel 316L connectors and valves (Hamlet, Israel), and glass made compensation tanks. The device is assembled in an incubator (37° C., 5% $CO_2$) and is monitored by means of both pressure (#742 Mennen Medical, USA) and flow monitors (#T106 Transonic Systems Inc., USA). The data obtained is analyzed by a data acquisition system, which presents the calculated values of the shear forces produced inside the grafts on-line.

Once the device is assembled (clean and sterile before each experiment), the pressure and flow connectors are connected to the system and to the monitors, which are calibrated. The data acquisition software is activated and the system is filled with warm (37° C.) growth medium (M199, Penicillin (200 unit/ml)-Streptomycin (0.2 mg/ml), Amphothericin (0.5 microgram/ml) and fetal calf serum (FCS), 20%). Two PTFE grafts are then fitted onto the stainless steel connectors and secured in place with silicone strings. Pulsatile flow of medium in the system is slowly increased through adjustment of the stroke volume and flow rate of the pump. The fluid runs in the system in stainless steel and Teflon® tubing. A physiological pulse wave is generated using tank A. Control of the fluid wave is achieved with valve A. Valves B and C provide control of the fluid flow through the grafts. Pressure in the system is controlled by valve D. Equilibration of the system with the atmosphere in the incubator is achieved by compensation tank B, which also serves as a fluid reservoir.

Endothelial cells retention on an e-PTFE graft was examined following EC transduction with retroviruses encoding for the UP50, VEGF-GFP genes and native EC. Grafts seeded with EC over-expressing UP50 were tested against grafts seeded with EC expressing GFP. The results show that ECs over-expressing UP50 are retained much better than cells that express GFP when exposed to arterial-like flow and shear stress. No difference was observed when EC seeded grafts transduced with GFP were compared to graft seeded with native ECs. Retention of grafts seeded with EC over-expressing UP50 were also compared to grafts seeded with ECs over-expressing VEGF. The ECs over-expressing UP50 showed superior retention to those over-expressing VEGF. Retention of cells on a graft seeded with EC over-expressing UP50 and VEGF was compared to that on a graft seeded with EC over-expressing only VEGF. The cells over-expressing both factors showed substantially better retention that cells over-expressing VEGF alone.

To examine whether the above in vitro results would be duplicated in vivo, grafts seeded with sheep autologous ECs over-expressing cell proliferation growth factor and cell adhesion factor were implanted in donor sheep arteries (Example 26). The results showed that grafts seeded with cells over-expressing either UP50-GFP or VEGF-GFP had a higher number of cells adhering to the grafts following exposure to in vivo blood flow compared to cells over-expressing GFP only. In addition, grafts seeded with cells over-expressing UP50 displayed higher number of adherent cells than the grafts seeded with cells over-expressing GFP or VEGF.

Artificial vascular grafts of this invention may be used in place of any current by-pass or shunting graft, either natural or artificial, in any application. Thus, they may be used for, without limitation, arterial by-pass, both of the cardiac variety and that used to treat peripheral arterial disease (PAD). An artificial graft of this invention may also be used as a replacement or substitute for a fistula created for use in hemodialysis. Also the synthetic artificial vascular graft of the present invention can be used to replace a damaged blood vessel such as traumatically damaged limb arteries.

A presently preferred application for a graft of the present invention is an artificial arteriovenous shunt for use by dialysis patients.

In hemodyalysis, a patient's blood is "cleansed" by passing it through a dialyzer, which consists of two chambers separated by a thin membrane. Blood passes through the chamber on one side of the membrane and dialysis fluid circulates on the other. Waste materials in the blood pass through the membrane into the dialysis fluid, which is discarded, and the "clean" blood is re-circulated into the blood stream. Access to the bloodstream can be external or internal. External access involves two catheters, one placed in an artery and one in a vein. More frequently, and preferably, internal access is provided. This is accomplished either by an artriovenous fistula or an AV graft. An AV fistula involves the surgical joining of an artery and a vein under the skin. The increased blood volume stretches the elastic vein to allow for a larger volume of blood flow. Needles are placed in the fistula so that blood can be withdrawn for dialysis and then the blood is returned through the dilated vein.

An AV graft may be used for people whose veins, for one reason or another, are unsuitable for an AV fistula. An AV graft involves surgically grafting a donor vein from the patient's own saphenous vein, a carotid artery from a cow or a synthetic graft from an artery to a vein of the patient. One of the major complications with a synthetic AV graft is thrombosis and neointimal cell proliferation that cause closure of the graft.

To counter thrombosis and neointimal proliferation, grafts have been seeded with a patient's own endothelial cells. However, the high rate of blood flow through these grafts together with the damage caused by the incursion of needles through the layer of cells often results in the detachment of the ECs from the walls of the graft. The grafts of the present invention overcome this deficiency.

In the first place, the genetically altered ECs of this invention, which over-express UP50 and VEGF, are more capable of remaining attached to the graft at the site of puncture thus minimizing damage caused by the needle. Furthermore, the altered cells proliferate more rapidly than native ECs and thus cover the puncture site more quickly and completely. This reduces exposure of the ECM, other substances used to enhance the performance of the graft and the graft material itself to blood, which would be expected to reduce the occurrence of thrombosis at site of puncture. Rapid regeneration of the EC layer should also reduce SMC proliferation at site of anastamosis and will thus improve patency of the graft in the shunt. This is demonstrated in Example 27.

Thus, cells genetically altered to express or over-express endothelial proliferation growth factor and cell adhesion factor are substantially more resistant to the shear forces of blood flow and have a higher capacity to cover completely grafts even after mechanical damage or shear stress induced detachment. In addition, it has been found that cells that have been genetically altered to express or over-express VEGF and UP50 appear to cover and repair the damage caused by punctures much more rapidly than cells that do not express these factors. Thus, grafts of the present invention should also have a lower occurrence of thrombosis at the site of needle invasion into the graft or at a bare surface of the graft. These factors should result in substantially greater patency than current grafts and a longer useful lifetime in a patient.

EXAMPLES

The following examples are provided solely to illustrate various aspects of the present invention. They are not intended, nor are they to be construed, to limit the scope of the invention in any manner whatsoever.

The examples that follow employ nomenclature and procedures used generally in the molecular, biochemical, microbiological and recombinant DNA arts. See, for example, "Molecular Cloning: A laboratory Manual," Sambrook et al. (1989); "Current Protocols in Molecular Biology," Volumes I-III, Ausubel, R. M., ed. (1994); Ausubel, et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" ($8^{th}$ Edition), Appleton & Lange, Norwalk, Conn. (1994); Mishell and Shiigi (eds), "Selected Methods in Cellular Immunology", W. H. Freeman and Co., New York (1980); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R.

I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996) and U.S. Pat. Nos. 4,666,828; 4,683,202; 4,801,531; 5,192,659 and 5,272,057; 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521. The U.S. patents are incorporated by reference, including any drawing, as if fully set forth herein.

Example 1

Generation of Recombinant Adenoviral Vectors Encoding the LacZ Gene

A 3700 bp HindIII-BamHI fragment containing the bacterial β-galactosidase gene LacZ (Clontech, Calif., USA) was inserted into plasmid pCA3 for constitutive expression under the control of the CMV immediate-early promoter. The resultant plasmid was co-transfected with plasmid pJM17 into "293" cells that constitutively express the adenoviral E1 gene. Plasmid pJM17 contains the adenovirus genome, excluding the E3 region, and including an insert (pBRX) in the E1 region of the virus. Homologous recombination between pCA3 encoding β-galactosidase and pJM17 following transfection replaced the E1 region of pJM17 with the CMV-β-galactosidase expression cassette from pCA3. Plaque formation occurred 2 to 4 weeks following co-transfection, after which individual plaques were isolated and viral extracts were amplified therefrom by infection of "293" cells. The titer of each viral stock was determined by plaque assay in "293" cells. Viral titers of $\sim 10^{10}$ pfu/ml were obtained. Expression of β-galactosidase by infected cells was confirmed by X-gal staining.

Example 2

Generation of Recombinant Bicistronic Adenoviral Vectors Encoding the VEGF and GFP Genes A 600 bp BamHI fragment containing the human $VEGF_{165}$ cDNA (Genbank Accession number AB021221), including the signal sequence for secretion (gift of Dr. J. Abraham, Scios Nova, Mountain View, Calif.) was inserted into the BglII site of shuttle vector pQBI-CMV5-GFP (QBI, Canada), thereby generating shuttle vector CMV5-$VEGF_{165}$-IRES-EGFP (FIG. 3a). The expression plasmid pQBI-CMV5-GFP contains the left arm (16%) of the Ad5 genome with a deletion in the E1 region containing an hCMV5 insert. Shuttle vector CMV5-$VEGF_{165}$-IRES-EGFP was co-transfected with plasmid pJM17 into "293" cells constitutively expressing the E1 gene. The pJM17 plasmid contains the adenovirus genome, excluding the E3 region, and including an insert (pBRX) in the E1 region of the virus. Recombination between CMV5-IRES-$VEGF_{165}$-GFP and pJM17 following transfection replaced the E1 region and pBRX insert with the expression cassette from CMV5-IRES-$VEGF_{165}$-GFP. Plaque formation occurred 2 to 4 weeks following co-transfection after which individual plaques were isolated and viral extracts were amplified by infection of "293" cells. The titer of each viral stock was determined by plaque assay in "293" cells. Titers of $\sim 10^{10}$ pfu/ml were obtained. Transgene expression was confirmed by Western blot analysis of infected, cell-conditioned medium.

Example 3

Generation of Pseudotyped Retroviral Vectors Encoding Human VEGF and GFP

Recombinant retroviral vectors encoding the GFP and human $VEGF_{165}$ genes were constructed by cloning into plasmid pLXSN (# K1060-B Clontech, USA) in two steps. First, a 600 bp BamHI fragment encoding $VEGF_{165}$ (Genbank Accession number AB021221) was inserted into the BamH1 site of plasmid pIRES2-EGFP (#6029-1 Clontech). Then, a 2.0 kB EcoRI-MunI fragment containing the $VEGF_{165}$, IRES and EGFP encoding sequences was cloned into the EcoRI restriction site in pLXSN resulting in vector LXSN-$VEGF_{165}$-IRES-EGFP (FIG. 3b). For retroviral vector production, 293E3 ecotropic packaging cells were transiently transfected with LXSN-$VEGF_{165}$-EGFP. After 48 hours, the supernatant from confluent cultures of G418-resistant producer cells was collected, filtered (0.45 μm) and used to transduce PA317 amphotropic packaging cells. Transduced PA317 cells were grown under G418 (Gibco, BRL USA) selection (300 mg/ml) and after 48 hours the supernatant was collected and used to transduce TEFLYGA packaging cells which express GALV envelope glycoprotein to generate pseudotyped virus capable of transducing ECs and SMCs with high efficiency. After G418 selection (400 μg/ml) of transduced TEFLYGA cells, individual colonies were collected and screened for EGFP and $VEGF_{165}$ expression. Viral titers of each colony were determined by TE671 cell transduction and were found to range from $10^5$ to $10^6$ pfu/ml. The highest-titer producing colonies were selected and freshly collected supernatants were employed for transduction.

Example 4

Generation of Recombinant Adenoviral Vectors Encoding the UP50 Gene

Recombinant adenoviral vector expressing the human UP50 gene (obtained from Y. Shaul, Weizmann Institute) was constructed as described above. A 1361 bp BglII fragment containing the human UP50 cDNA (SEQ. ID No. 1) was inserted into plasmid pCA3. Transgene-containing plasmid pCA3 was co-transfected with plasmid pJM17 into "293" cells. Homologous recombination between the expression plasmid and pJM17 following transfection replaced the E1 region with the expression cassette from the pCA3 plasmid thereby generating shuttle vector CMV5-UP50 (FIG. 4a). Plaque formation occurred 2-4 weeks following co-transfection. Individual plaques were isolated and viral extracts were amplified by infection of 293 cells. Titers of viral stock of $\sim 10^{11}$ pfu/ml were obtained. Transgene expression was confirmed by Western blot analysis of infected cell-conditioned medium.

Example 5

Generation of Recombinant Adenoviral Vectors Encoding Both the UP50 and GFP Genes A recombinant adenoviral vector co-expressing human UP50 and GFP genes was constructed via a modified AdEasy protocol (28). A 1361 bp BglII fragment of UP50 cDNA was inserted into the BgIII site pAdTrack-CMV shuttle vector under the control of the CMV promoter. The shuttle vector encodes GFP under the control of an additional CMV promoter downstream to the transgene. Insert-containing shuttle vector was linearized by PmeI digestion and purified using a Qiaquick gel extraction kit (Qiagen, Germany). Competent BJ5183 cells were co-transfected with insert-containing shuttle vector and pAdEasy-1 by electroporation and positive clones containing recombinant adenoviral vector encoding UP50-GFP (FIG. 4b) were selected by PCR and restriction map analysis. Recombinant adenoviral plasmids were linearized by PacI digestion, purified and transfected into "293" cells using Lipofectamine 2000 (Gibco BRL, USA). Seven days following transfection, cytopathic effect occurred and 100% of the cells were found to express GFP. The cells were harvested and viral extracts were further amplified in "293" cells. The titer of each viral stock was determined by serial dilution assay in "293" cells and the titers of ~$10^{11}$ pfu/ml were obtained. Expression of transgene was confirmed by Western blot analysis of infected cell-conditioned medium.

Example 6

Construction of Retroviral Vectors for Expression of UP50 or co-expression of UP50 and EGFP Recombinant retroviral vector LXSN-UP50 encoding the human UP50 gene (FIG. 4c) was constructed by inserting the human UP50 cDNA 1361 bp BgIII fragment into the BamHI site of plasmid pLXSN (# K1060-B Clontech, USA) under the control of Mo-MULV 5' long terminal repeat (LTR).

A bicistronic recombinant retroviral vector encoding both the UP50 and EGFP genes was cloned into plasmid pLXSN in two steps. First, a 1400 bp IRES-EGFP EcoRI-HpaI fragment excised from pIRES2-EGFP (Clontech, #6029-1) was inserted into EcoRI-HpaI-digested pLXSN for construction of the control plasmid pLXSN-IRES-EGFP. Next, pLXSN-UP50-IRES-EGFP (FIG. 4d) was constructed by cloning human UP50 EcoRI fragment (1361 bp) into the EcoRI site of pLXSN-IRES-EGFP. Gene expression in these constructs is regulated by Mo-MULV 5' long terminal repeat (LTR).

Example 7

Generation of Pseudo-Typed Recombinant Retroviral Vectors Encoding UP50

For retroviral vector production, vector pLXSN-UP50-EGFP or pLXSN-UP50 was transfected into 293FLYA packaging cells using Lipofectamine (Gibco BRL, USA). After 48 hours, supernatant from confluent cultures of viral producer cells was collected, filtered (0.45 µm) and added to 293FLY10A or 293 FLYGALV packaging cells. Transduced cells were grown under G418 selection (400 µg/ml) and individual colonies were collected and screened for EGFP expression using an inverted fluorescent microscope. They were also screened for UP50 expression by Western blot analysis of transduced cell-conditioned medium. The viral titer of each colony was determined via transduction of TE671 cells and titers of ~$10^6$ ffu/ml were obtained. Supernatant from colonies with the highest-titers was collected freshly for transduction of EC and SMC.

Example 8

Tissue Culture of Primary Vascular Cells

Human saphenous vein ECs (HSVEC), human radial artery ECs (HRAEC) and human left internal mammary artery ECs (HLAEC) were harvested from 5 cm-long vascular segments by collagenase digestion, as previously described (29). Isolated ECs were cultured on gelatin-coated dishes containing M199 medium (Gibco BRL, USA) supplemented with 20% fetal calf serum (hyClone, USA), 2 mM L-glutamine (Biological Industries, Israel), 100 units/ml penicillin (Biological Industries, Israel), and 0.1 mg/ml streptomycin (Biological Industries, Israel), 100 µg/ml heparin (Sigma, USA) and 2 ng/ml bFGF (obtained from Prof. Neufeld). Cells from passages 3-9 were collected to ensure phenotypic stability, which was monitored on the basis of cellular morphology and by immunohistochemical staining for von Willebrand factor and CD31. Human SMCs were cultured by ex-plant outgrowth from human saphenous veins, human radial artery (HRASMC) and left internal mammary arteries (HLSMC). Cells were cultured in Dulbecco's Modified Eagles Medium (DMEM) (Gibco BRL, USA) supplemented with 10% pooled human serum, 2 mM L-glutamine, 100 units/ml penicillin, 0.1 mg/ml streptomycin and 2 ng/ml bFGF. SMCs were identified by immunohistochemical staining for smooth muscle α-actin (Dako, USA). Cells were routinely tested for sterility, endotoxins and mycoplasma infection. Animal veins were excised from minipigs and sheeps using the same procedures as with human vascular segments. The ECs and SMCs from both pigs and sheep were likewise harvested in the same manner as human ECs and SMCs.

Example 9

Tissue Culture of Cell Lines

The packaging cell lines 293-FLYA, 293-FLY10A, 293-FLYGALV and TEFLYGA (obtained from Dr. F. L. Cosset-Lion, France) were grown in DMEM supplemented with 10% FCS (Biological Industries, Israel), 2 mM L-glutamine, 100 units/ml penicillin, 0.1 mg/ml streptomycin, 6 µg/ml blasticidin (Sigma, USA) and 6 µg/ml phleomicin (Sigma, USA).

The packaging cell lines PA317, 293E3 (obtained from Dr. J. Exelrod, Haddasa, Jerusalem) were grown in DMEM supplemented with 10% FCS, 2 mM L-glutamine, 100 units/ml penicillin and 0.1 mg/ml streptomycin. Cells were routinely tested for sterility, endotoxins, and mycoplasma contamination.

Example 10

Infection of EC and Vascular SMC with Recombinant Adenoviral Vectors

Cells were seeded at 70% confluence on fibronectin (Sigma, USA) pre-coated plates (4.5 µg/ml) 20 hours prior to infection and grown in complete medium (M20). On the day of infection, the culture medium was replaced with fresh serum-free M199 medium and recombinant virus was added at a multiplicity of infection (MOI) of 3000 (i.e., 3000 viral particles/cell). The cells were incubated for 90 minutes with gentle tilting every 20 minutes after which the virus-containing medium was replaced with complete medium (M20). The infection rate was monitored by visualization of GFP expression using a fluorescent inverted microscope (TE200 Nikon, Japan) equipped with a fluorescent GFP filter (GFP-LP, Nikon).

Example 11

Transduction of EC and SMC with Recombinant Retroviral Vectors

EC or SMC (passage 4-9) were seeded at $10^5$ cells/35-mm well in plates coated with 4.5 µg/ml fibronectin and grown in complete medium for 24 hours. The cells were pre-conditioned one hour prior to transduction by replacement of the culture medium with serum-free M199 medium containing 0.1 mg/ml DEAE-dextran (Sigma, USA). Following pre-conditioning, the cells were washed three times with phosphate-buffered saline (PBS). Transduction was performed by a 4 h incubation of the cells with supernatant freshly collected and filtered (0.45 µl) from virus-producing packaging cells. At the end of the incubation the virus-containing medium was replaced with M20 medium.

Example 12

Seeding of PTFE Grafts with EC

A PTFE graft (Gore co. USA) was aseptically cut to the required length, washed three times in PBS (30 min at room temperature) and incubated in fibronectin (20 µg/ml in PBS overnight, 37° C.). Two connectors (Teflon or stainless steel) were inserted, one into each side of the graft. The connectors were secured by silicon strings tied in three double knots. Each graft end is corked with a rubber cap.

Cells were trypsinized and centrifuged at 1200 rpm, for 5 min. The pellet was re-suspended in growth medium at a cell density equivalent to 400,000 cells/cm$^2$ of graft. HEPES buffer 10 mM pH 7.3 was added to the cell suspension.

Grafts were aseptically mounted on the central axis of the seeding tube and filled with the cell suspension using a Pasteur pipette. The grafts were examined for leaks and the central axis was then inserted into the surrounding tube, which was filled with growth medium containing HEPES buffer 10 mM. The tube was sealed and placed in an incubator (5% $CO_2$, 37° C.) where it was rotated at ⅙ rpm for 2 hr. Then, the rubber corks were aseptically removed and rotation continued for an additional 2 hours. The grafts were transferred from the seeding device to culture plates containing growth medium supplemented with bFGF 2 ng/ml and incubated (5% $CO_2$, 37° C.) for 48 hours. The efficiency of graft seeding was evaluated by fluorescence microscopy detection of GFP production by seeded cells or by histochemical hematoxylin-eosin staining.

Example 13

Endothelial Cell Quantitative Morphometry

At the end of the incubation period, the grafts were fixed in 4% paraformaldehyde for 1 hour. Following fixation, the grafts were cut longitudinally, examined under fluorescent microscope, photographed and the images processed by an image analysis system (Image pro Plus, Media cybernetics USA). Morphometric evaluation of endothelial seeded grafts was performed by computerized image analysis to evaluate surface covering of the graft by the endothelial cells. The image analysis system consists of a digital video camera (DXM1200 Nikon, Japan) installed on a fluorescent inverted microscope (TE200 Nikon, Japan). The data is digitized and transferred to an image analysis system (Image Pro Plus 4 image analysis software). At least ten fields were selected by random movement of the graft under the microscope (at ×100 magnification) of the graft surface were analyzed. The analysis included determination of the ratio of endothelial cell coverage area to whole field area (Per-area) as using the image analysis software. Each field was divided to 12 equal quadrants and the same ratio was determined for each quadrant.

In addition, a subjective assessment was performed by scoring the observed homogeneity (scale of 1-3) and density (scale of 1-5) of coverage.

Example 14

Detection of Transgene Expression in Genetically Modified Vascular Cells

Total RNA was isolated from ECs and SMCs 48 hours after transformation with UP50-encoding adenoviral and retroviral vectors, using a PURESCRIPT RNA isolation kit (Gentra systems, USA). RNA concentration was calculated from the absorbance at 260 nm.

For cDNA synthesis, 1 µg of RNA was mixed with 500 ng random hexamers, the mixture was heated at 70° C. for 10 minutes and then cooled on ice. A mixture of 0.4 mM dNTPs, 5 units AMV-reverse transcriptase (RT) (Promega), 5 mM DTT, 32 units RNAse-out (Gibco BRL) and RT buffer (Promega) was added to the RNA. The reaction mixture was then incubated for 2 hours at 38° C. followed by 15 minutes at 95° C. PCR was performed in a volume of 50 µl with 7 µl of reverse transcriptase (RT) reaction mix, 20' pmole of sense primer:

```
                                          (SEQ ID NO: 2)
  5'-GAAGATCTTGACATGCCAGGAATAAAAAGGATACTC-3',
```

20 pmol of anti-sense primer:

```
                                          (SEQ ID NO: 3)
  5'-GAAGATCTTCAGAATGGGTACTGCGACACATATATCCGCAGTCG-3',
```

240 mmol dNTPs, 1U Ex-Taq DNA polymerase (Takara, Japan) and reaction buffer (Takara). The PCR cycling protocol was: 94° C. for 2 minutes followed by 10 cycles of 94° C./30 sec->50° C./30 seconds->72° C./60 sec. This was followed by 21 cycles of: 94° C./30 seconds->60° C./30 seconds->72° C./60 seconds+5 seconds/cycle->72° C./10 min. RT-PCR products were analyzed by electrophoresis on 1% agarose gel.

Example 15

Western Immunoblot Analysis of UP50 and VEGF Protein Expression

Expression of UP50 or VEGF protein by adenovirally or retrovirally altered ECs and SMCs was detected by Western blot analysis of altered cell-conditioned medium. Culture medium was replaced with serum-free medium 24 hours post-alteration and the cells were cultured for an additional 24 hours. Samples of the altered-cell conditioned medium (CM)

(30 μl) were separated by electrophoresis in 10% SDS polyacrylamide gel under reducing conditions. Separated protein was electroblotted onto a nitrocellulose membrane (Schleicher & Schuell). The blots were blocked with incubation blocking solution (TBS containing 0.1% skim milk and 0.3% Tween-20 (TBST)) for 1 hour at room temperature with gentle agitation. Afterwards, the blots were incubated with primary antibody diluted in blocking solution for 2 hours at room temperature. Affinity purified polyclonal rabbit anti-UP50 antibody (#9855, custom made, Sigma, Israel) (1:5000) was used for UP50 detection, and polyclonal rabbit anti-VEGF$_{165}$ antibody (#SC 152 Santa-Cruz, USA) (1:700) was used for VEGF detection.

Following incubation with primary antibody, the blots were washed three times with TBST and incubated with anti-rabbit peroxidase-conjugate secondary antibody (Sigma, USA) diluted with TBST for 1 hour at room temperature. After three washes with TBST, specific protein was visualized by development of blots with ECL reagents (Sigma, USA) and exposure to X-ray film.

Example 16

Immunohistochemical Analysis of UP50 Expression

Adenovirally-infected EC and SMC were seeded on chamber slides (Lab-Tek, USA) pre-coated with fibronectin (4.5 μg/ml), and cultured for 24 hours. Cells were fixed 48 hours following adenoviral infection by incubation at room temperature for 20 minutes in 4% paraformaldehyde followed by two washes with PBS. The cells were denatured by heating the slides with 1 mM EDTA, pH 8.0, in a microwave oven for 5 minutes. The samples were blocked using blocking solution supplied with the Histostain-Plus kit (Zymed, USA) according to manufacturer's instructions. After blocking, the cells were incubated with affinity-purified anti-UP50 (1:50) for 1 hour at room temperature. The samples were washed 3 times with PBS-T (PBS containing 0.3% Tween-20) and incubated for one hour with rhodamine-conjugated goat anti-rabbit IgG antibody (#SC 2091, Santa Cruz, USA) diluted 1:400 in PBS-T. The cells were washed 3 times with PBS-T and covered with mounting medium (H-1000, Vector laboratories, USA). Samples were then visualized by fluorescence scanning confocal (MRC-1024, BioRad) microscopic detection of GFP and rhodamine in the cells.

For immunohistochemical analysis of UP50 in the ECM, ECs infected with recombinant adenoviral vector encoding the UP50 gene were induced to generate ECM by addition of dextran to the growth medium. After denudation of the EC layer using 20 mM NH$_4$OH solution, the ECM was subjected to rhodamine-based immunostaining using anti-UP50 antibody.

Example 17

UP50 and VEGF Protein Expression by Co-Cultures of Adenovirally-Infected ECs and SMCs Adenovirally-infected ECs or mixes of adenovirally-infected ECs and SMCs were cultured for 24 hours following infection in serum-supplemented medium followed by an additional 24 hours in serum-free medium. Supernatant proteins were separated electrophoretically on 10% SDS polyacrylamide gel and the separated proteins were electroblotted onto nitrocellulose membranes. Blots were incubated with anti-VEGF or anti-UP50 antibodies. Following exposure to peroxidase-conjugated secondary antibody, the blots were developed with ECL reagents and exposed to X-ray film.

Example 18

Western Blot Analysis of VEGF and UP50 Protein Expression by Co-Cultures of Retrovirally-Infected EC and SMC ECs infected with different retroviruses or mixtures of infected ECs and SMCs were cultured in serum-supplemented medium for 24 hours following infection after which the cells were cultured in serum-free medium for an additional 24 hours. Samples of the growth medium (30 μl) were separated on a 10% SDS polyacrylamide gel and electroblotted onto a nitrocellulose membrane. Blots were incubated with either anti-VEGF or anti-UP50 antibodies. Following exposure to a peroxidase-conjugated secondary antibody the blots were developed with ECL reagents and exposed to X-ray film.

Example 19

Functional Analysis of Over-Expressed Recombinant VEGF and UP50 in Vascular Cells Endothelial cells (passages 5-11) were seeded at 30% confluence ($10^4$ cells/well) in 24-well plates pre-coated with 4.5 μg/ml fibronectin 24 hours prior to adenoviral infection. The cells were infected with Ad.UP50-GFP, Ad.GFP or Ad.VEGF$_{165}$-GFP. Following 90 minutes of exposure to adenoviral vectors at 37° C., serum-containing medium was added and 16-18 hours later the medium was substituted with M199 medium containing 2% human serum and 2 ng/ml bFGF. Assays were performed in triplicate and proliferation was measured by XTT colorimetric assay on day 7 following infection.

Example 20

Adhesion of EC to ECM Generated by UP50-Over-Expressing EC

ECs were seeded on fibronectin pre-coated 48 well plates ($10^4$ cells/well) 24 hours before infection. The cells were infected with Ad.UP50-GFP or Ad.GFP, as previously described. After infection the cells were grown in M20 medium supplemented with 4% dextran 42000 (Sigma USA) for 7 days. Following this infection period, the culture medium was aspirated from the infected cells and the matrix producing cells were denuded by contact with 20 mM NH$_4$OH for approximately 5 minutes. After cell lysis ECM-coated wells were washed three times with PBS and stored in PBS at 4° C.

ECs were detached by incubation in 10 mM EDTA solution, the matrix was washed with M199 medium and incubated in culture medium (CM) from Ad.UP50-GFP infected, Ad.GFP infected, or non-infected ECs for 15 minutes. Following incubation, ECs were seeded on the ECM coated wells ($2\times10^4$ cell per well). The cells seeded on ECM generated by Ad.UP50-GFP infected EC were incubated in CM from Ad.UP50-GFP infected cells. Cells seeded on ECM generated by Ad.GFP infected cells were incubated with CM collected from Ad.GFP infected cells and the control group of cells seeded on ECM generated by non-infected cells were incubated with non-infected cell-conditioned medium. The cells were incubated for an additional 30 minutes to allow cell adhesion and were then washed with PBS. Quantitation of the remaining adherent cells was performed via XTT colorimetric assay.

Similar experiments were performed utilizing ECM generated from retroUP50-GFP transduced EC.

Example 21

Effect of UP50 on EC Growth in Three-Dimensional Collagen Culture—in-vitro Angiogenesis In vitro angiogenesis in collagen gels was quantitated using adenovirus infected EC spheroids. The generation of EC spheroids was performed as previously described (33). Endothelial cells were suspended in culture medium containing 0.25% (w/v) carboxymethylcellulose and cultured in non-tissue culture-treated round-bottomed 96-well plates (Nunc, Denmark) for 24 h at 37° C., 5% $CO_2$, during which time the suspended cells formed a single spheroid per well of defined size and cell number (~750 cells/spheroid). The spheroids were then embedded in collagen gels. Collagen stock solution was prepared prior to use by mixing 8 volumes of acidic rat tail collagen extract (equilibrated to 2 mg/ml, 4° C.), 1 volume 10×M199 (Gibco BRL, USA). The pH was adjusted to 7.4 by addition of 0.34N NaOH. To prevent sedimentation of spheroids before polymerization of the collagen gel, 1 volume of collagen stock solution was mixed with 1 volume of room temperature M199 medium containing 40% human serum and 0.5% (w/v) carboxymethylcellulose. Spheroid-containing gels (20-30 spheroids/gel) were rapidly transferred into pre-warmed 24-well plates and allowed to polymerize. The gels were incubated at 37° C. with 5% $CO_2$ and proliferation of ECs in the gels was documented by photomicrography using a digital video camera (DXM1200 Nikon, Japan). The sprouting of at least 40 spheroids from each group was analyzed.

Example 22

Effect of UP50 Over-Expression on Adhesion of in Vitro-Cultured EC Following Trypsinization Endothelial cells were seeded at 70-80% confluence (6-7.5×$10^4$ cells/well) in 12 well plates, 24 hours prior to adenoviral infection. The cells were infected (3×$10^3$ pfu per cell), as previously described, with Ad.UP50-GFP or Ad.GFP. Non-infected cells served as control. After infection the cells were grown in M20 medium for 4 days. The cells were washed with PBS and adhesion assay was performed by trypsinization of the cells using 0.0025% trypsin containing 0.001% EDTA. After 3 minutes incubation at room temperature, trypsin was neutralized by addition of complete medium (M20). The cells were washed three times with PBS and then M20 (300 µl) medium was added to the cells. Quantitation of the remaining adherent cells, as percent of control non-trypsinized cells, was determined via colorimetric XTT assay.

Example 23

Effect of UP50 Over-Expression on Cell Adhesion to ECM

ECs were detached by 10 mM EDTA solution, washed with M199 medium containing 0.1% BSA (Sigma, USA), 10 mM HEPES, and incubated with the culture medium (CM) from Ad.UP50-GFP or Ad.GFP infected or from non-infected EC for 15 minutes. After incubation, the cells were seeded in the ECM coated wells (2×$10^4$ cell per well). The cells seeded oh ECM generated by Ad.UP50-GFP infected EC, were incubated in CM from Ad.UP50-GFP infected cells. Cells seeded on ECM generated by Ad.GFP infected cells were incubated with CM collected from Ad.GFP infected cells and the control group of cells seeded on ECM generated by non-infected cells were incubated with non-infected cell-conditioned medium. The cells were incubated for additional 30 minutes to allow cell adhesion and were then washed with PBS. Quantitation of the remaining adherent cells was performed by colorimetric XTT assay.

Figure 7:
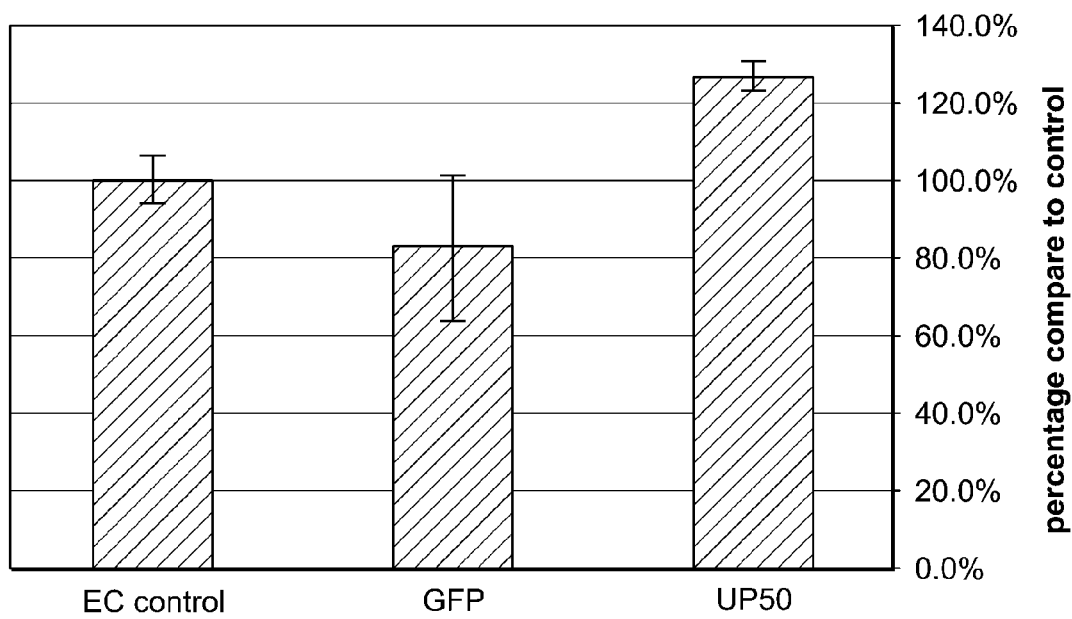
FIG. 7: histogram derived from an adhesion assay of ECs to UP50-containing extra-cellular matrix (ECM). Results are presented as corrected OD values after subtraction of background.

Exposure to secreted UP50 and to ECM-bound UP50 resulted in >30% increased adhesion of EC in comparison to the control group (FIG. 7).

Example 24

Effect of UP50 Over-Expression on Retention of EC under Continuous Shear Stress Human saphenous vein ECs (passage 8-11) were seeded ($10^5$ cells per 35 mm well) and grown in M20 up to 60-80% confluence. The cells were infected with Ad.UP50-GFP or Ad.GFP (MOI 3000) as described previously. Non-infected cells served as the control. The cells were grown for 30 hours to ensure transgene expression before exposure to shear stress. Prior to the experiment, two wells from each group (Ad.UP50-GFP, Ad.GFP, Control) were harvested using trypsin-EDTA and cells were counted. To cover the cells completely during rocking, 5 ml of M20 medium were added to each well. The plates were placed on a rocking table inside a $CO_2$ incubator and incubated for 20-24 hours with intense rocking (approximately 140 cycles/minute). Following rocking, the cells were washed 5 times with PBS. Cells were harvested using trypsin-EDTA and were counted by hemacytometer. The assay was also performed with cells transduced using retroviral vectors respectively.

The results demonstrate that UP50 overexpression by retroviral-transduction results in increased adherence of EC exposed to continuous shear stress. Ninety-eight percent of the UP50-expressing cells 98% remained adhered to the plate in contrast to the GFP-expressing (72%±1%) and non-transduced ECs (69±2%). Similar results were obtained with EC adenovirally-infected to express UP50.

Example 25

Retention of Human EC on ePTFE Grafts under Pulsatile Flow

Grafts were seeded as described above.

Each graft is subjected to a steady pressure of 120/80 mmHg and flow of 300 ml/minute for 2 hours. The grafts are then removed from the device and cell stability and adhesion to the graft are evaluated as described.

Seeded grafts were exposed to laminar flow conditions. The flow was adjusted to reach physiological blood pressure of 120/75 (mean of 90 mm Hg) for two hours at flow rate of 300 ml/min using 60 pump strokes per minute. The grafts were evaluated by microscopy and morphometric analysis. After exposure to flow conditions, evaluation of cell density and homogeneity on the graft inner surface was performed. The grafts were fixed in freshly prepared 4% paraformaldehyde in PBS at room temperature for 1 hour. The grafts were cut open, flattened between two glass slides, viewed under a fluorescent microscope and analyzed using morphometric analysis as previously described. Complementarily, the grafts were stained with hematoxylin-eosin and analysed as previously mentioned.

Example 26

Retention of Genetically Modified EC Seeded onto Artificial Vascular Grafts under in Vivo Flow Conditions; Short-Term Implantation of ePTFE Grafts Coated with Genetically Modified Sheep EC in Sheep Arteries Small caliber ePTFE grafts (6 mm) were seeded with sheep EC that were genetically modified by retroviral transduction to over-express GFP, UP50-GFP or $VEGF_{165}$-GFP 36 hours prior to implantation.

Fasting (12 hours) adult sheep were pre-medicated with 10 mg diazepam injected intramuscularly and 500-600 mg of intravenously administered sodium pentobarbital. They were then intubated and anesthesia was maintained with inhaled 1%-2% isoflurane. Aspirin (600 mg) was administered pre-operatively. The monitoring system during the experiment included blood pressure measurement, pulse oxymetry, and ECG. Heparin (300 U/kg) was injected intravenously for systemic anticoagulation following exposure and preparation of arteries for graft implantation. Blood samples were taken during the procedure every 30 minutes to assess the efficacy of heparinization by measuring partial thromboplastin time (PTT).

The seeded grafts were then implanted bilaterally end to side in sheep carotid and femoral arteries by an expert cardiac surgeon. On one side of the femoral artery the implanted graft was seeded with retroGFP transduced ECs and on the other side the implanted graft was seeded with retroUP50-GFP transduced ECs (femoral arteries). In the femoral artery on one side the implanted graft was seeded with $retroVEGF_{165}$-GFP transduced EC and on the other side the implanted graft was seeded with retroUP50-GFP transduced EC. Patency of the implanted grafts was assessed 30 minutes following exposure of the implanted grafts to blood flow and prior to graft harvesting by direct palpation, flow measurements using a Doppler flow meter (Transonic Animal Research Flowmeter, N.Y., USA) and by performing selective angiography.

Flow rates through the femoral grafts were similar on both sides (~50 ml/min, 38% of femoral blood flow). The flow through the carotid grafts, which was higher at the beginning of the experiment, was bilaterally diminished at the end of two hours due to local thrombosis at the anastomosis site (secondary to surgical complications). The femoral and carotid grafts were harvested two hours following implantation. Both grafts were then harvested and cellular retention on the interior surfaces of the grafts was analyzed by fluorescence microscopy.

Following graft removal, sheep were sacrificed by intravenous potassium chloride administration. All experiments were performed according to animal care and experimentation laws of the Technion ITT, Haifa, Israel.

Example 27

Recovery of Genetically Modified EC Over-Expressing UP50 and VEGF Seeded onto Artificial Vascular Grafts Subjected to Dialysis Needle Puncture ePTFE grafts were seeded with genetically modified ECs over-expressing UP50 and VEGF and ECs over-expressing GFP. Twenty-fopur hours after seeding, the grafts were mounted on the outer surface with Matrigel (2 mg/ml) and then were punctured with a 14G needle used in dialysis. The grafts were incubated for 24 hours and then visualized using fluorescent microscopy. Grafts seeded with UP50 and VEGF showed enhanced proliferation and bridging across punctures of endothelial cells closing the gap in the needle track. Grafts seeded with ECs over-expressing GFP did not exhibit this effect. Closure of the gap produced by the needle provide a biocompatible surface to the graft and hence reduce local thrombosis.

---

What is claimed is:

1. A method of performing hemodialysis on a patient, comprising:
    (a) providing a synthetic tubular element comprising a first end, a second end, an exterior surface, and an interior surface that describes a lumen;
    (b) coating an adhesion matrix on the interior surface;
    (c) providing a plurality of endothelial cells seeded and cultured on the interior surface of the tubular element, wherein the endothelial cells are genetically altered to express or over-express a full-length human fibulin-5 polypeptide;
    (d) implanting the synthetic tubular element under the skin of the patient, wherein, the first end of the tubular element is grafted into an artery and the second end of the tubular element is grafted into a vein, such that, fluidic continuity is established from the artery through the lumen of the tubular element and into the vein; and,
    (e) operatively coupling the lumen of the tubular element to a hemodialysis filtration unit such that blood is diverted from the lumen into the hemodialysis filtration unit and then is returned to the lumen.

2. The method of claim 1, wherein the endothelial cells are also genetically altered to express or over-express one or more cell proliferation growth factors.

3. The method of claim 2, wherein the cell proliferation growth factor is VEGF.

4. The method of claim 1 further comprising, following step (c) and prior to step (d):
    coating of adhesion matrix on the exterior surface of the tubular element; and
    providing a plurality of smooth muscle cells seeded and cultured on the exterior surface of the tubular element, wherein the smooth muscle cells are genetically altered to express or over-express one or more cell adhesion factors and one or more cell proliferation growth factors.

5. The method of claim 4, wherein the cell proliferation growth factor is VEGF.

* * * * *

SEQUENCE LISTING

```
<160> NUMBER OF SEQ ID NOS: 3

<210> SEQ ID NO 1
<211> LENGTH: 1347
<212> TYPE: DNA
<213> ORGANISM: Homo sapiens

<400> SEQUENCE: 1
atgccaggaa taaaaaggat actcactgtt accattctgg ctctctgtct tccaagccct      60
gggaatgcac aggcacagtg cacgaatggc tttgacctgg atcgccagtc aggacagtgt     120
ttagatattg atgaatgccg aaccatcccc gaggcctgcc gaggagacat gatgtgtgtt     180
aaccaaaatg gcgggtattt atgcattccc cggacaaacc ctgtgtatcg agggccctac     240
tcgaacccct actcgacccc ctactcaggt ccgtacccag cagctgcccc accactctca     300
gctccaaact atcccacgat ctccaggcct cttatatgcc gctttggata ccagatggat     360
gaaagcaacc aatgtgtgga tgtggacgag tgtgcaacag attcccacca gtgcaacccc     420
acccagatct gcatcaatac tgaaggcggg tacacctgct cctgcaccga cggatattgg     480
cttctggaag gccagtgctt agacattgat gaatgtcgct atggttactg ccagcagctc     540
```

```
tgtgcgaatg ttcctggatc ctattcttgt acatgcaacc ctggttttac cctcaatgag      600
gatggaaggt cttgccaaga tgtgaacgag tgtgccaccg agaacccctg cgtgcaaacc      660
tgcgtcaaca cctacggctc tttcatctgc cgctgtgacc caggatatga acttgaggaa      720
gatggcgttc attgcagtga tatggacgag tgcagcttct ctgagttcct ctgccaacat      780
gagtgtgtga accagcccgg cacatacttc tgctcctgcc ctccaggcta catcctgctg      840
gatgacaacc gaagctgcca agacatcaac gaatgtgagc acaggaacca cacgtgcaac      900
ctgcagcaga cgtgctacaa tttacaaggg ggcttcaaat gcatcgaccc catccgctgt      960
gaggagcctt atctgaggat cagtgataac cgctgtatgt gtcctgctga gaaccctggc     1020
tgcagagacc agcccttttac catcttgtac cgggacatgg acgtggtgtc aggacgctcc     1080
gttcccgctg acatcttcca aatgcaagcc acgacccgct accctggggc ctattacatt     1140
ttccagatca aatctgggaa tgagggcaga gaattttaca tgcggcaaac gggccccatc     1200
agtgccaccc tggtgatgac acgccccatc aaagggcccc gggaaatcca gctggacttg     1260
gaaatgatca ctgtcaacac tgtcatcaac ttcagaggca gctccgtgat ccgactgcgg     1320
atatatgtgt cgcagtaccc attctga                                         1347

<210> SEQ ID NO 2
<211> LENGTH: 36
<212> TYPE: DNA
<213> ORGANISM: Artificial sequence
<220> FEATURE:
<223> OTHER INFORMATION: Chemically synthesized primer

<400> SEQUENCE: 2
gaagatcttg acatgccagg aataaaaagg atactc                                36

<210> SEQ ID NO 3
<211> LENGTH: 44
<212> TYPE: DNA
<213> ORGANISM: Artificial sequence
<220> FEATURE:
<223> OTHER INFORMATION: Chemically synthesized primer

<400> SEQUENCE: 3
gaagatcttc agaatgggta ctgcgacaca tatatccgca gtcg                        44
```